US012766172B2

(12) United States Patent
Kim et al.

(10) Patent No.: US 12,766,172 B2
(45) Date of Patent: Oct. 20, 2026

(54) **COMPOSITION FOR PREVENTING, TREATING, OR IMPROVING GASTROINTESTINAL DISEASES COMPRISING STRAIN OF GENUS *CORYNEBACTERIUM* AND CULTURE THEREOF**

(71) Applicant: CJ CheilJedang Corporation, Seoul (KR)

(72) Inventors: Yang-Su Kim, Seoul (KR); Nahum Lee, Seoul (KR); Young Gi Hong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 721 days.

(21) Appl. No.: 17/618,942

(22) PCT Filed: Jun. 2, 2020

(86) PCT No.: PCT/KR2020/007169
§ 371 (c)(1),
(2) Date: Dec. 14, 2021

(87) PCT Pub. No.: WO2020/251208
PCT Pub. Date: Dec. 17, 2020

(65) Prior Publication Data

US 2022/0378854 A1 Dec. 1, 2022

(30) Foreign Application Priority Data

Jun. 14, 2019 (KR) ........................ 10-2019-0071007

(51) Int. Cl.

| | |
|---|---|
| ***A61K 35/741*** | (2015.01) |
| ***A61K 9/00*** | (2006.01) |
| ***A61K 31/198*** | (2006.01) |
| ***A61P 1/04*** | (2006.01) |
| ***A61P 31/04*** | (2006.01) |

(52) U.S. Cl.
CPC .......... *A61K 35/741* (2013.01); *A61K 9/0056* (2013.01); *A61K 31/198* (2013.01); *A61P 1/04* (2018.01); *A61P 31/04* (2018.01)

(58) Field of Classification Search
None
See application file for complete search history.

(56) References Cited

U.S. PATENT DOCUMENTS

| | | | |
|---|---|---|---|
| 8,486,670 B2 | 7/2013 | Lee et al. | |
| 2004/0224036 A1 | 11/2004 | Bedding et al. | |
| 2009/0215133 A1 | 8/2009 | Bathe et al. | |
| 2012/0164698 A1 | 6/2012 | Wendisch et al. | |
| 2013/0302470 A1 | 11/2013 | Becker et al. | |
| 2014/0147522 A1 | 5/2014 | Normand et al. | |
| 2014/0356518 A1* | 12/2014 | Park ......................... | C12N 1/20 435/252.32 |
| 2017/0065647 A1 | 3/2017 | Kim et al. | |

FOREIGN PATENT DOCUMENTS

| | | | |
|---|---|---|---|
| CN | 101208427 | | 6/2008 |
| CN | 101946002 | | 1/2011 |
| CN | 102743754 | | 10/2012 |
| CN | 103224964 | | 7/2013 |
| CN | 104824363 | | 8/2015 |
| CN | 105796541 | | 7/2016 |
| EP | 0 416 892 | * | 3/1991 |
| JP | 47019087 | * | 9/1972 |
| JP | 2007-195543 | | 8/2007 |
| JP | 2007-525951 | | 9/2007 |
| JP | 2012214451 | | 11/2012 |
| JP | 2013-146247 | | 8/2013 |
| JP | 2019-011361 | | 1/2019 |
| KR | 20060018868 | | 3/2006 |
| KR | 20100053546 | | 5/2010 |
| KR | 20160094485 | | 8/2016 |
| KR | 10-1947945 | | 2/2019 |
| RU | 2588657 | | 7/2016 |
| WO | 2004108894 | | 12/2004 |
| WO | 2009005379 | | 1/2009 |
| WO | 2016-116585 | | 7/2016 |
| WO | WO 2018/149821 | * | 8/2018 |

OTHER PUBLICATIONS

EFSA panel. EFSA Journal, Jan. 2019, 17(2): 5601, pp. 1-13.*
Blazer M. "Helicobacter pylori and gastric disease". BMJ, Clinical Review 1998, vol. 316, pp. 1507-1510.*
EPO, Search Report of EP 20822031.9 dated Jun. 14, 2023. Centers for Diseases Control and Prevention, 'Other Sterilization Methods', Guideline for Disinfection and Sterilization in Healthcare Facilities, 2008, published on Dec. 10, 2017 Accessible version: https://www.cdc.gov/infectioncontrol/guidelines/disinfection/.
IP Australia, Office Action of the corresponding AU Patent Application No. 2020292062, dated Aug. 28, 2023.
Kipo, PCT Search Report & Written Opinion of PCT/KR2020/007169 dated Oct. 27, 2020.
Xiangbing Mao et al., "Specific roles of threonine in intestinal mucosal integrity and barrier function", Frontiers in Bioscience E3, 1192-1200, Jun. 1, 2011.

(Continued)

*Primary Examiner* — Vera Afremova
(74) *Attorney, Agent, or Firm* — LEX IP MEISTER, PLLC

(57) ABSTRACT

The present application relates to a composition for preventing, improving, or treating gastrointestinal diseases comprising a strain of the genus *Corynebacterium*, a culture thereof, and threonine. As the composition according to the present application is confirmed to have excellent anti-*Helicobacter pylori* efficacy in cell experiments, efficacy in improving gastrointestinal diseases in animal experiments, and efficacy in gastric mucus synthesis, the composition can be applied as a pharmaceutical composition for preventing or treating gastrointestinal diseases, as food for preventing or improving gastric ulcers, or as a composition for feed.

3 Claims, 15 Drawing Sheets
(6 of 15 Drawing Sheet(s) Filed in Color)

Specification includes a Sequence Listing.

(56) References Cited

OTHER PUBLICATIONS

Jeong Min An et al., "Anti-Helicobacter pylori, Anti-apoptotic, and Cytoprotective Effects of Threonine Synthesized from Corynebacterium glutamicum in Gastric Epithelial Cells", The Korean Journal of Helicobacter and Upper Gastrointestinal Research, 2019;19(4):245-256.
J.M. An et al., "Dietary Threonine Prevented Stress-Related Mucosal Diseases in Rats", Journal of Physiology and Pharmacology 2019, 70, 3, DOI: 10.26402/jpp.2019.3.xx.
Toru Miyamoto et al., "Inactivation of *Escherichia coli* Endotoxin by Soft Hydrothermal Processing", Applied and Environmental Microbiology, 75(15), 5058-5063.Aug. 2009, doi:10.1128/AEM.00122-09.
Makoto Ebisawa et al., "Heat-killed cell preparation of Corynebacterium glutamicum stimulates the immune activity and improves survival of mice against enterohemorrhagic *Escherichia coli*", Bioscience, Biotechnology, and Biochemistry,Jan. 30, 2017. http://dx.doi.org/10.1080/09168451.2017.1282804.
Law, G., "Threonine requirement and the effect of threonine on gut mucin characteristics in piglets receiving intragastric nutrition", Master thesis of university of Alberta. 1-143 (2000).
Lee I.H. (2018) Latest trend surrounding animal antimicrobial agents and alternatives. Pig & Consulting, 4, 70-73.
Huiliang Wen et al. "Production Technology of Biochemical Products" Jiangxi Science And Technology Press (Dec. 2004) p. 264.
Mao, Xiangbing, et al. "Specific roles of threonine in intestinal mucosal integrity and barrier function." Front Bioscience E3.(Jun. 1, 2011) pp. 1192-1200.
Nudel, Kathleen, et al. "Genomics of Corynebacterium striatum, an emerging multidrug-resistant pathogen of immunocompromised patients." Clinical Microbiology and Infection 24.9 (Jan. 9, 2018): 1016-e7-1016.e13.
Wittmann, Christoph, et al. "Metabolic fluxes in Corynebacterium glutamicum during lysine production with sucrose as carbon source." Applied and Environmental Microbiology 70.12 (Dec. 2004): 7277-7287.
El-Kersh, Karim, et al. "Predictive role of admission lactate level in critically ill patients with acute upper gastrointestinal bleeding." The Journal of emergency medicine 49.3 (Jun. 22, 2015): 318-325.
JPO, Office Action of the corresponding Japanese Patent Application No. 2021-574298 dated Jan. 31, 2023.
IP Australia, Office Action of the corresponding Australian Patent Application No. 2020292062 dated Mar. 30, 2023.
Rospatent, Office Action of the corresponding Russian Patent Application No. 2021136727 dated Mar. 23, 2023.
Rospatent, Office Action of the corresponding Russian Patent Application No. 2021136727 dated Aug. 26, 2022.
Maev I.V. et al. "Menetrier disease." Klinicheskaia Meditsina 93.4 (2015): 11-15.
Rogers E.A. et al. "Adhesion by pathogenic corynebacteria". Bacterial Adhesion, Advances in Experimental Medicine and Biology 715 (2011):91-103. doi: 10.1007/978-94-007-0940-9 6.
Jeong Min An et al., "Anti-Helicobacter pylori, Anti-apoptotic, And Cytoproective Effects of Threonine Alone or the Combination with Corynebacterum glutamicum in Gastric Epithelial Cells", Original Article to Korean J Gastroenterol, In English only excerpts, Nov. 7, 2019, total 25 pages.
Jeong Min An et al., "Dietary threonine and lignin prevented stress-related mucosal damages", Original Manuscript submitted to J Pharmacol Physiol, Jun. 28, 2019, total 15 pages.
Rospatent, the search report of Russian Patent Application No. 2021136727, dated Aug. 26, 2022, total 4 pages.
Vasileios Bampidis et al., "Safety and efficacy of I-threonine produced by fermentation with Corynebacterium glutamicum KCCM 80117 for all animal species", EFSA Journal 2019;17(2):5602, Feb. 28, 2019, total 13 pages.
Garson K. Law et al., "Adequate oral threonine is critical for mucin production and gut function in neonatal piglets", American Journal of Physiology-Gastrointestinal and Liver Physiology, 292(5), G1293-G1301, doi:10.1152/ajpgi.00221.2006, Jan. 18, 2007, total 9 pages.
Xiangbing Mao et al., "Specific roles of threonine in intestinal mucosal integrity and barrier function", Frontiers in Bioscience-Elite, E3(4), 1192-1200, https://doi.org/10.2741/e322, Jun. 1, 2011, total 9 pages.
IP India, Office Action of the corresponding IN Patent Application No. 202137061200., dated Dec. 18, 2025, total 10 pages.

* cited by examiner

【FIG. 1】
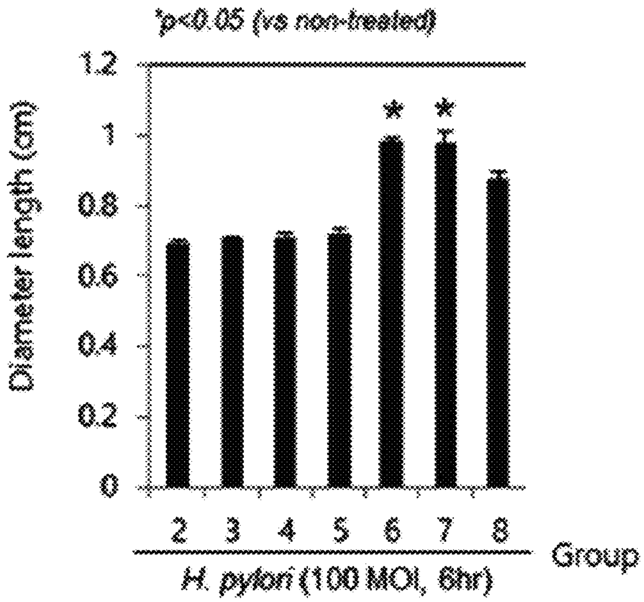
【FIG. 2a】
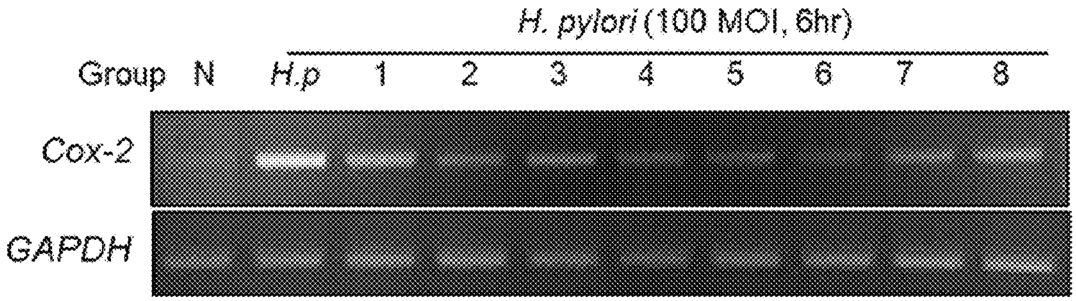
【FIG. 2b】
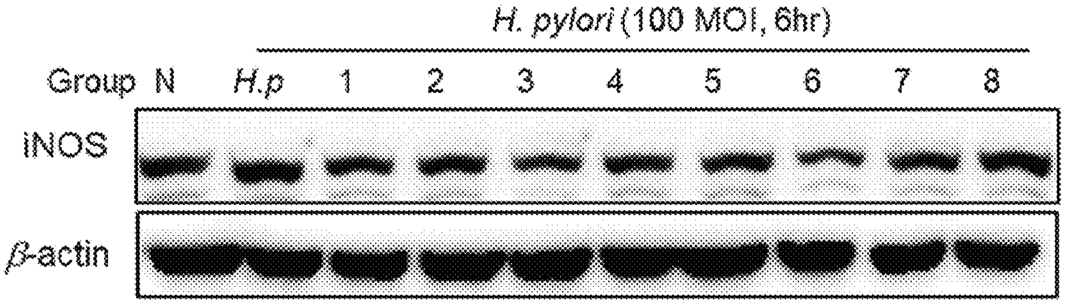

【FIG. 2c】
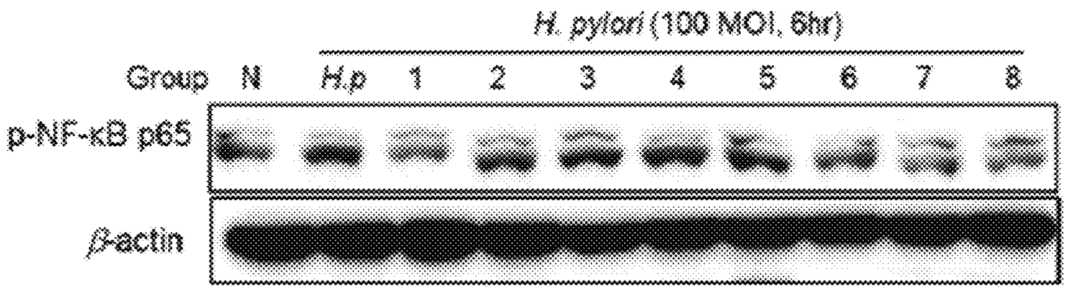
【FIG. 3a】
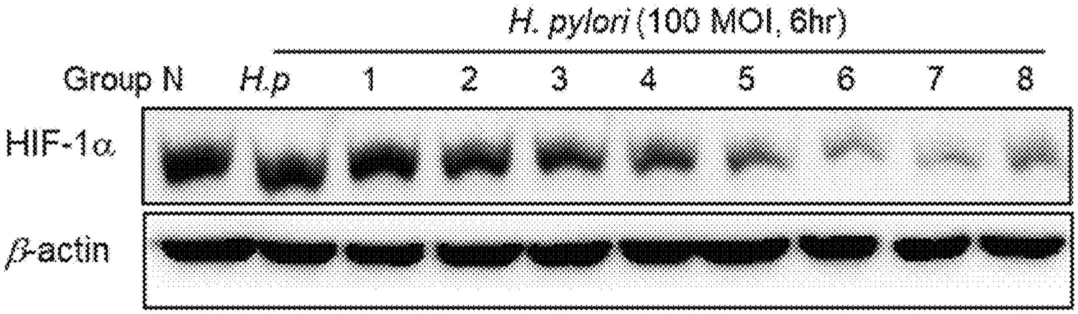

【FIG. 3b】
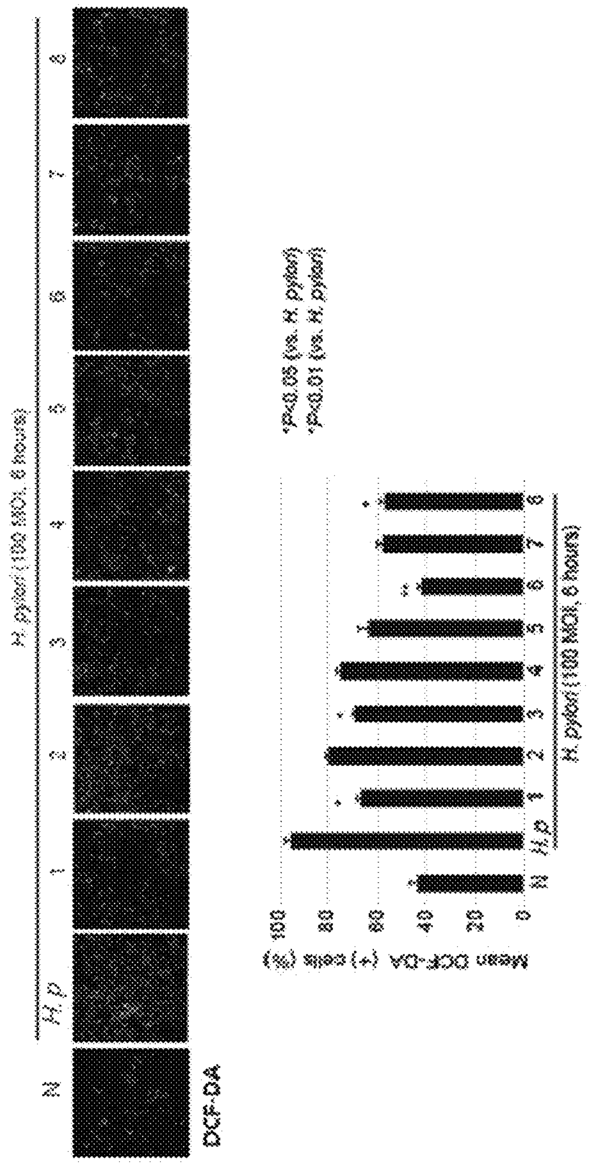

【FIG. 4a】
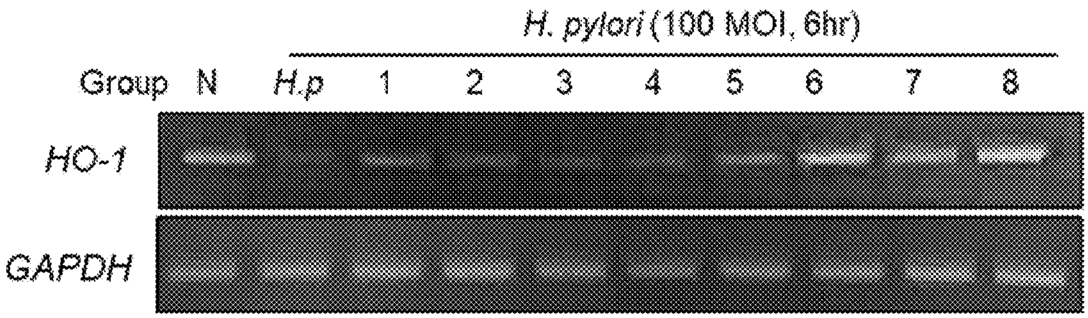
【FIG. 4b】
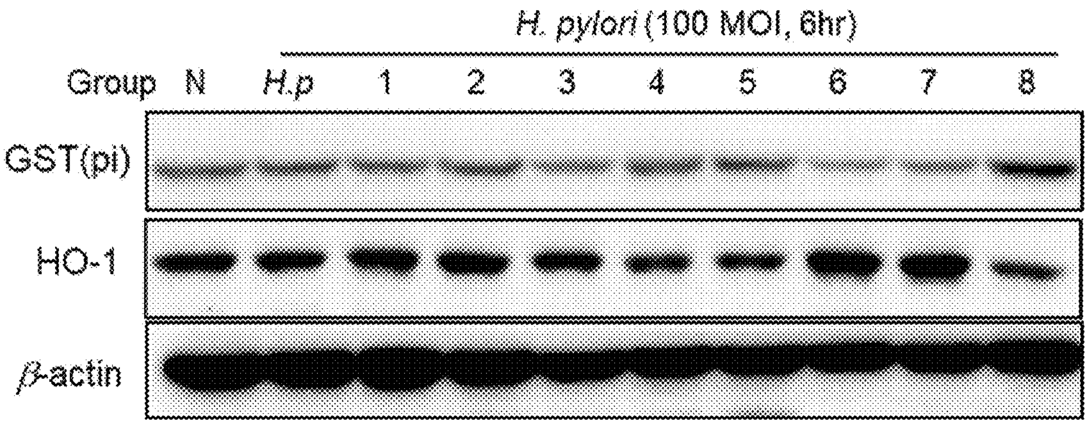
【FIG. 5a】
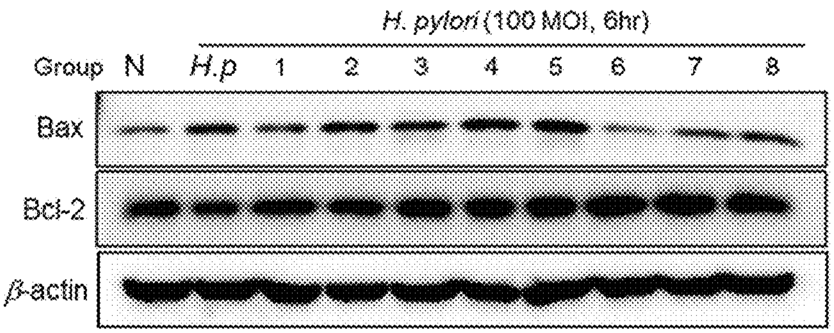

【FIG. 5b】
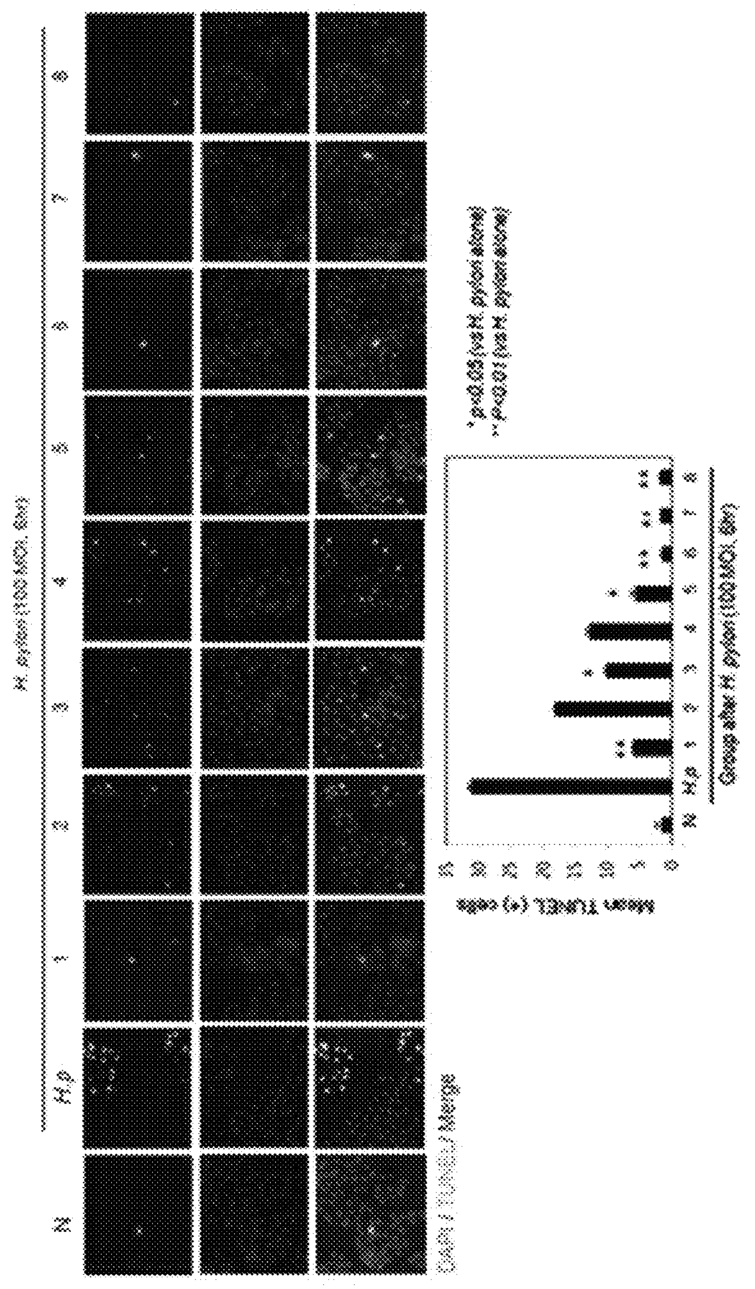

【FIG. 6a】
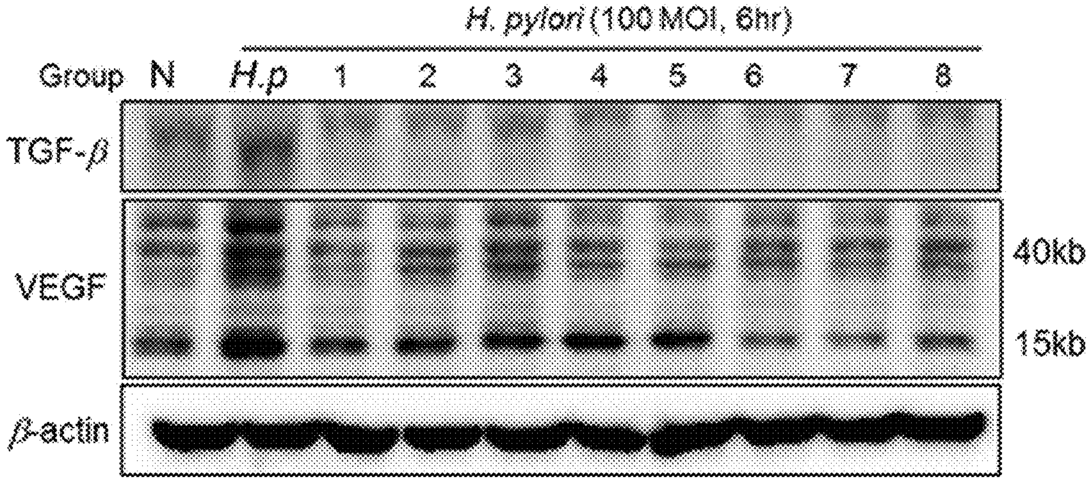
【FIG. 6b】
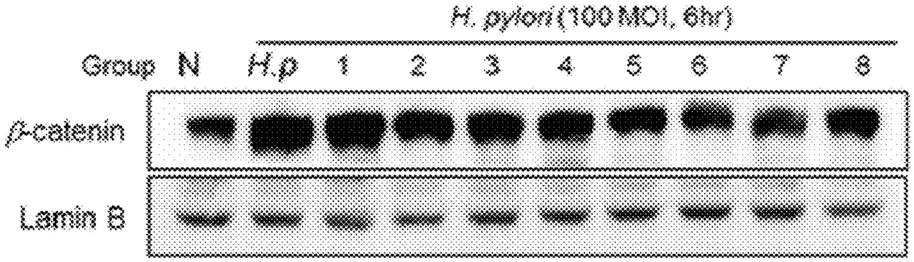

【FIG. 7a】
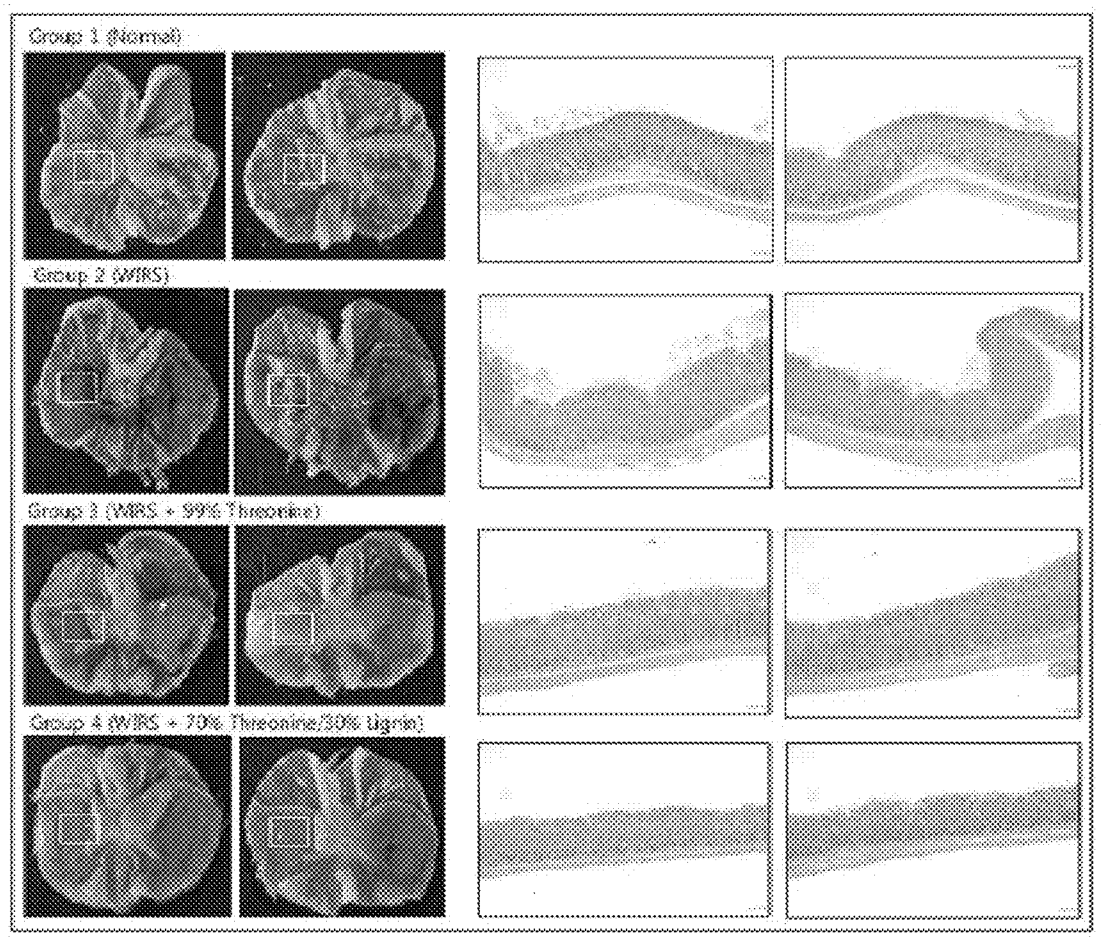

【FIG. 7b】
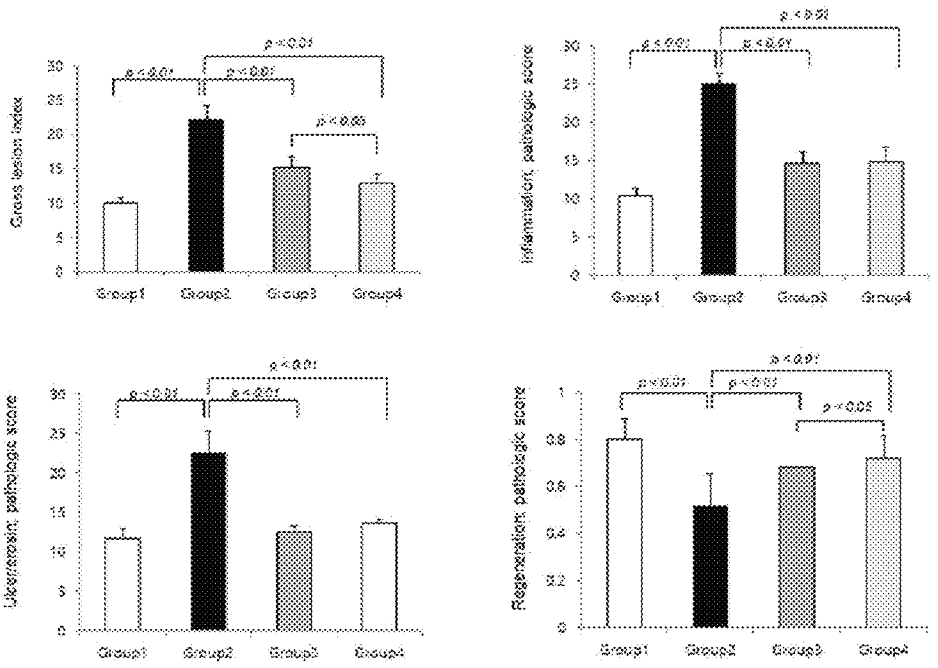
【FIG. 8a】
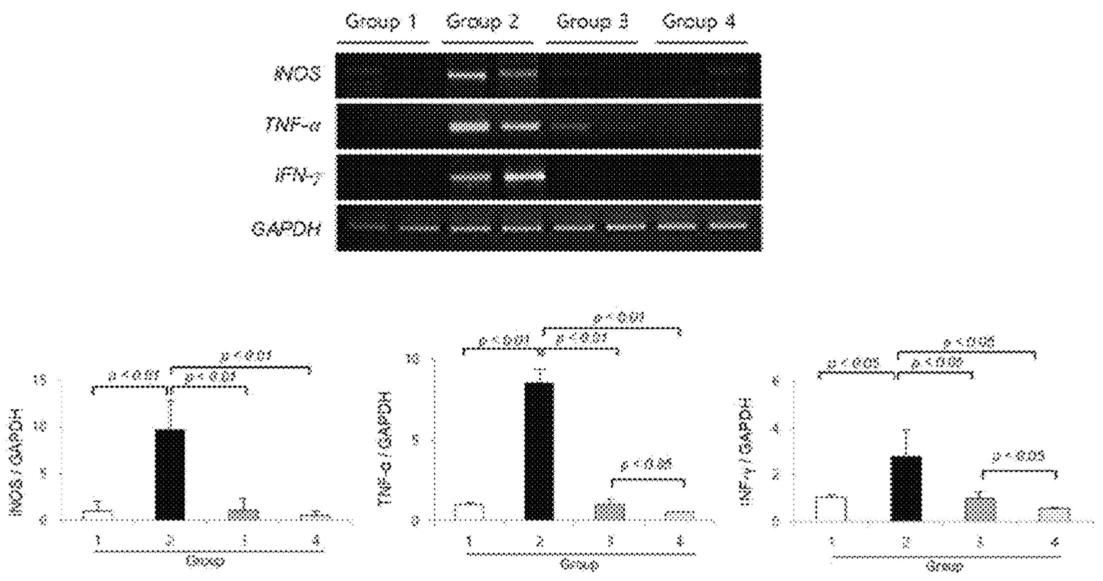

【FIG. 8b】
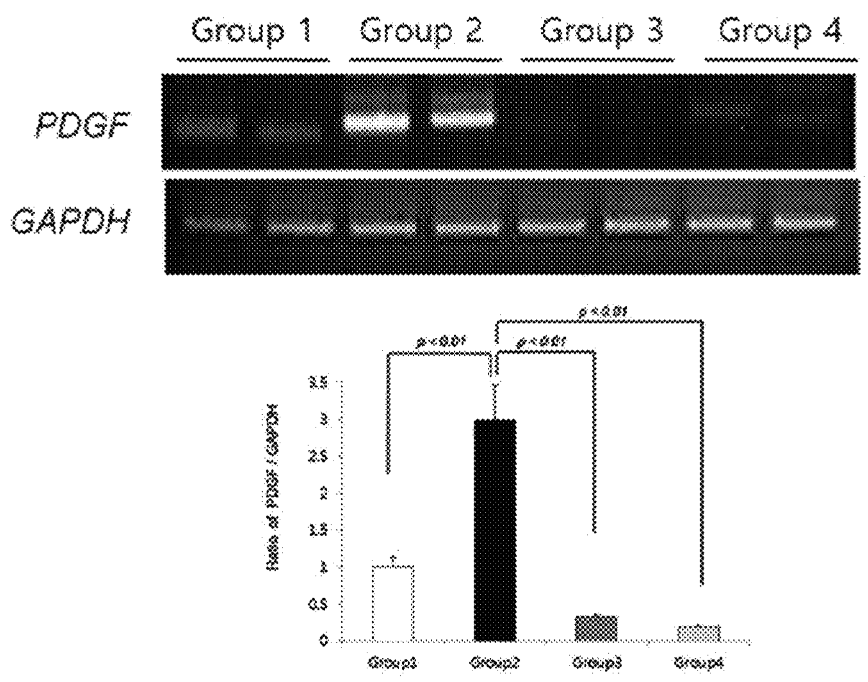
【FIG. 8c】
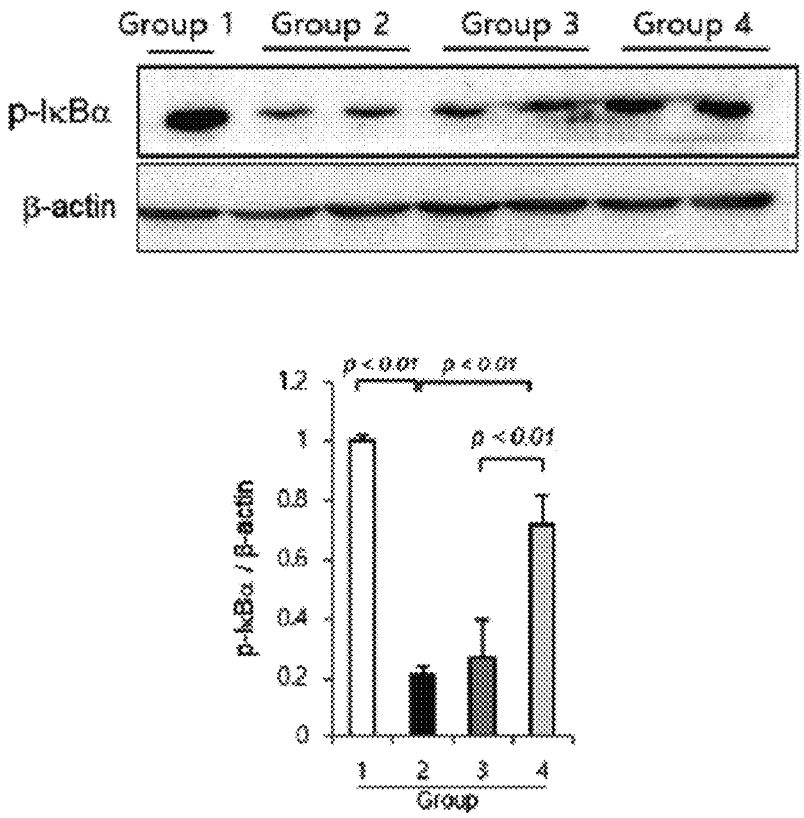

【FIG. 8d】
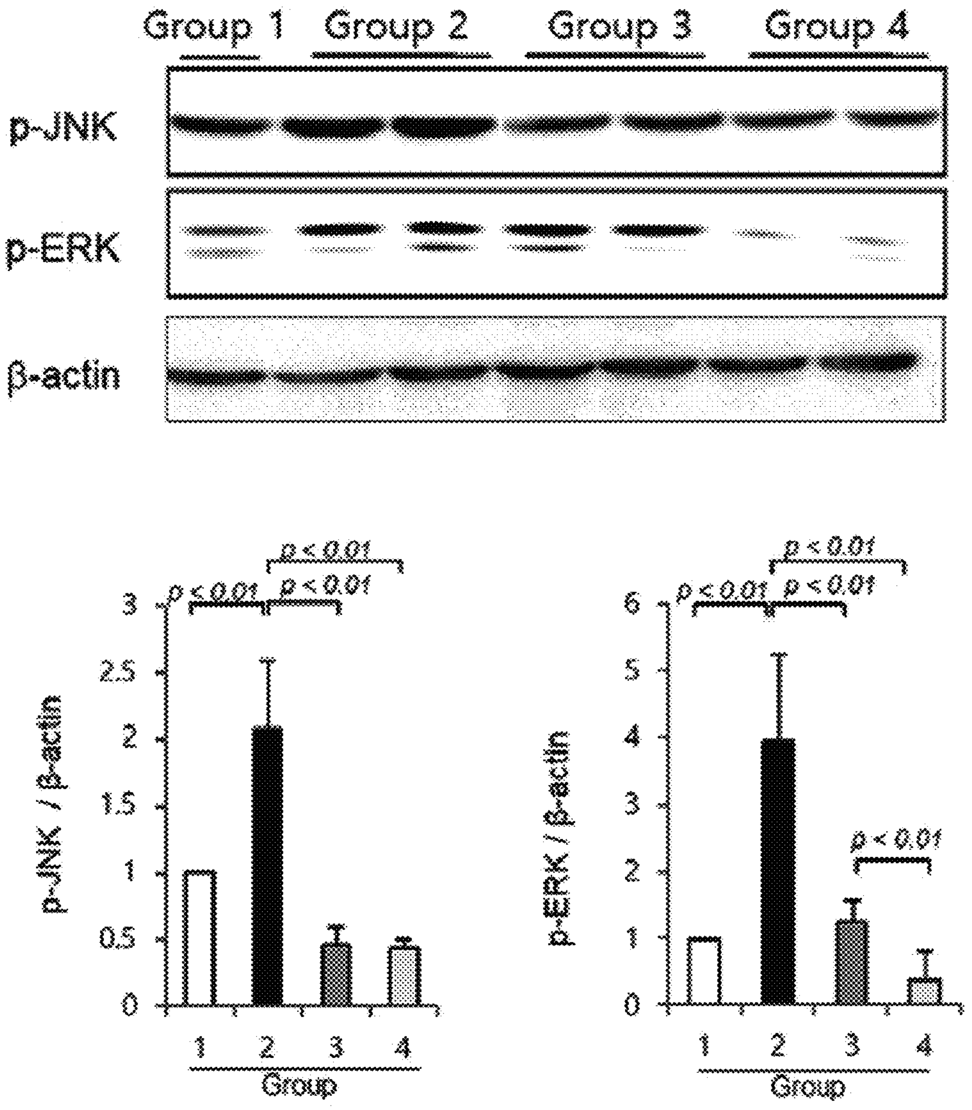

【FIG. 9a】
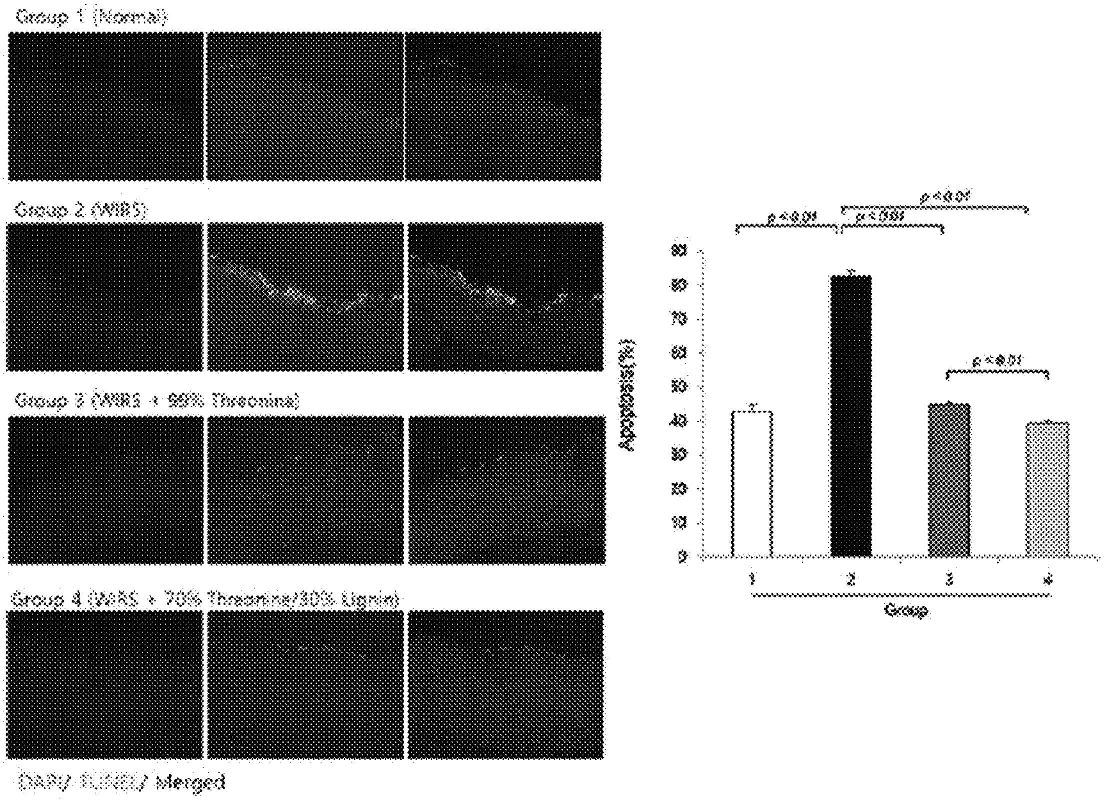

【FIG. 9b】
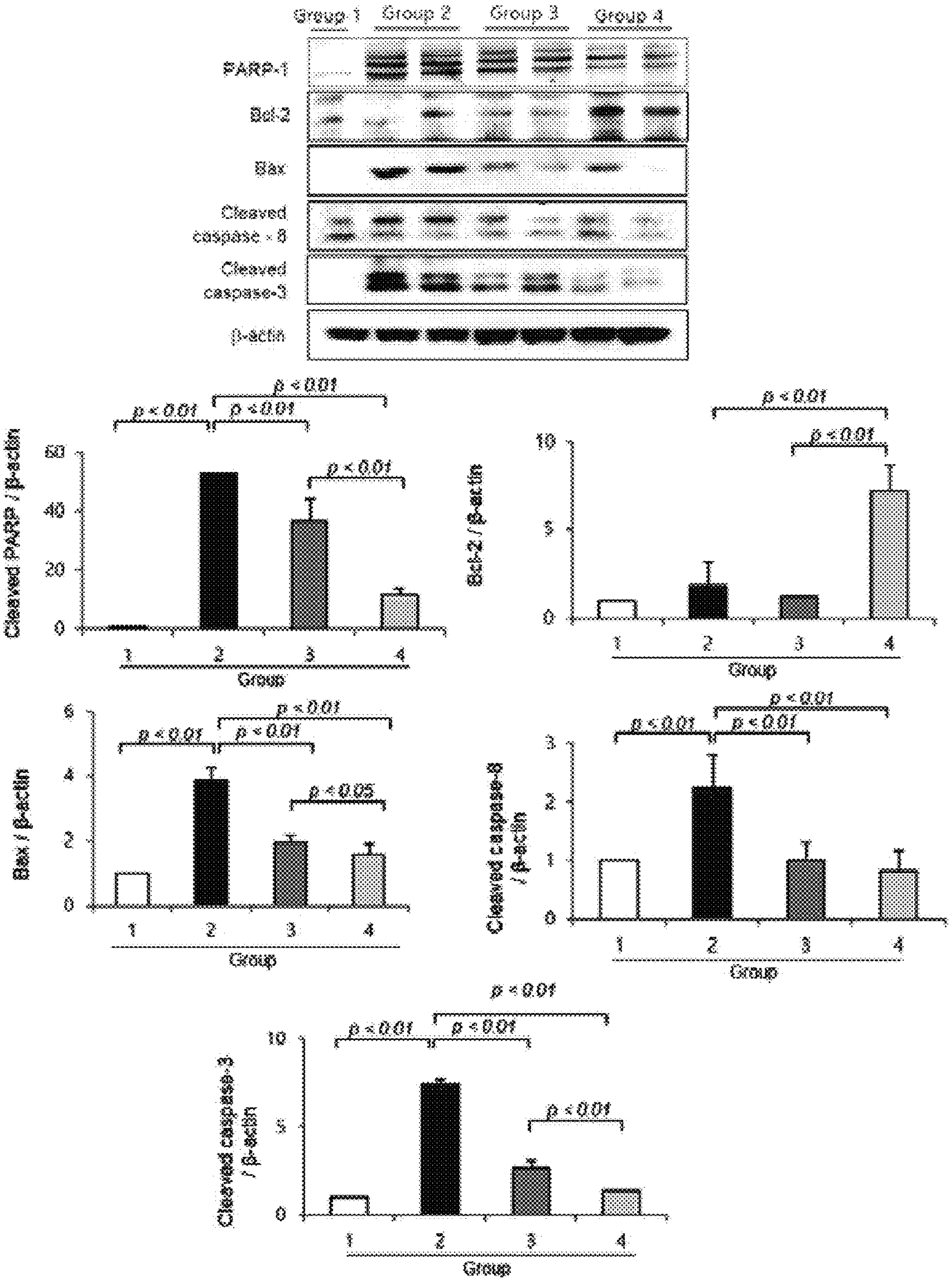

【FIG. 9c】
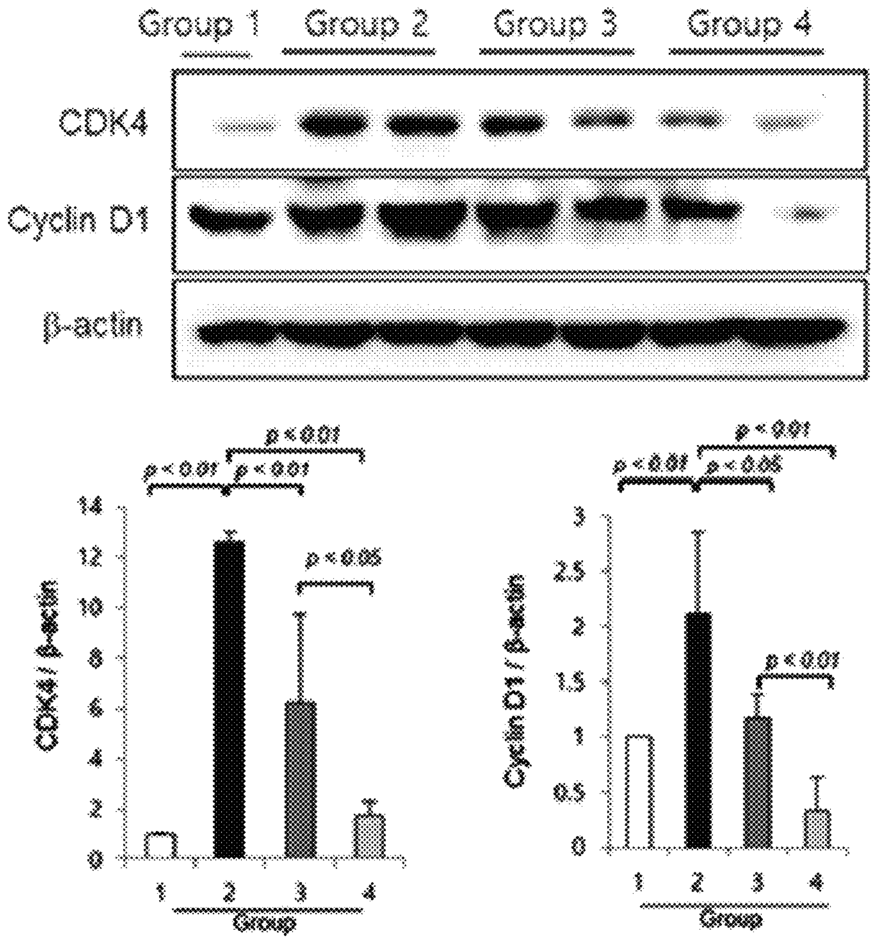

【FIG. 10】
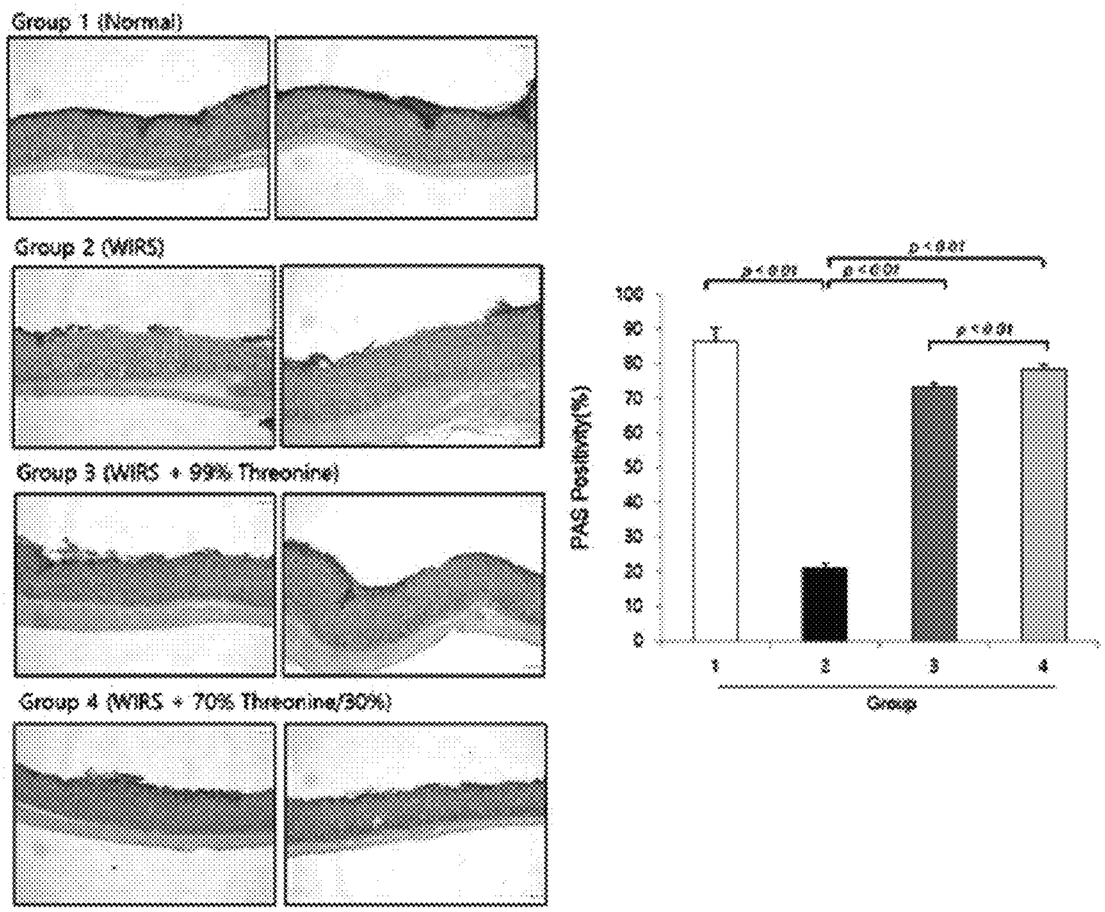

【FIG. 11】
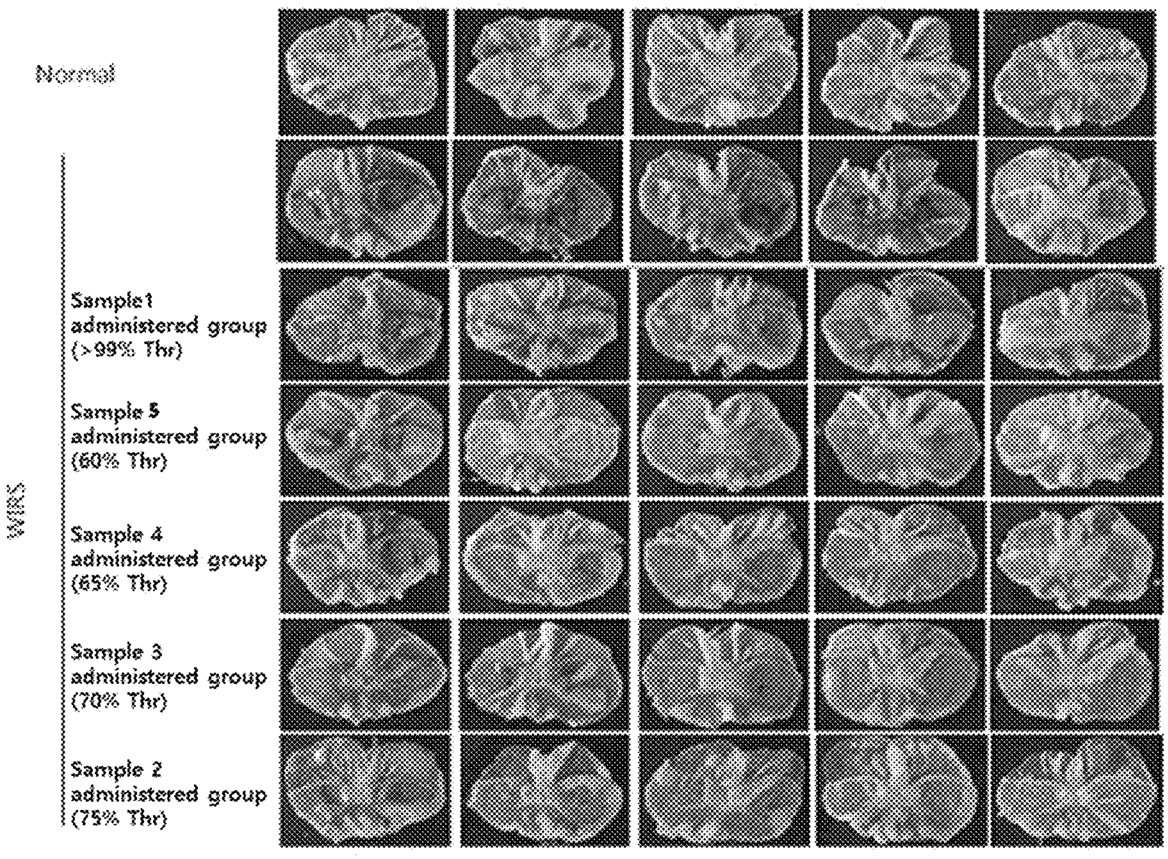

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial Sequence
```

<220> FEATURE:
<223> OTHER INFORMATION: Synthetic_IL-1beta_Forward

<400> SEQUENCE: 1
caggctccga gatgaacaac aaa 23

<210> SEQ ID NO 2
<211> LENGTH: 20
<212> TYPE: DNA
<213> ORGANISM: Artificial Sequence
<220> FEATURE:
<223> OTHER INFORMATION: Synthetic_IL-1beta_Reverse

<400> SEQUENCE: 2
tggggaactc tgcagactca 20

<210> SEQ ID NO 3
<211> LENGTH: 20
<212> TYPE: DNA
<213> ORGANISM: Artificial Sequence
<220> FEATURE:
<223> OTHER INFORMATION: Synthetic_IL-8_Forward

<400> SEQUENCE: 3
cagacagtgg cagggattca 20

<210> SEQ ID NO 4
<211> LENGTH: 20
<212> TYPE: DNA
<213> ORGANISM: Artificial Sequence
<220> FEATURE:
<223> OTHER INFORMATION: Synthetic_IL-8_Reverse

<400> SEQUENCE: 4
ttggggacac cctttagcat 20

<210> SEQ ID NO 5
<211> LENGTH: 20
<212> TYPE: DNA
<213> ORGANISM: Artificial Sequence
<220> FEATURE:
<223> OTHER INFORMATION: Synthetic_Cox-2_Forward

<400> SEQUENCE: 5
gaaatggctg cagagttgaa 20

<210> SEQ ID NO 6
<211> LENGTH: 20
<212> TYPE: DNA
<213> ORGANISM: Artificial Sequence
<220> FEATURE:
<223> OTHER INFORMATION: Synthetic_Cox-2_Reverse

<400> SEQUENCE: 6
tcatctagtc tggagtggga 20

<210> SEQ ID NO 7
<211> LENGTH: 20
<212> TYPE: DNA
<213> ORGANISM: Artificial Sequence
<220> FEATURE:
<223> OTHER INFORMATION: Synthetic_iNOS_Forward

<400> SEQUENCE: 7
ctcactggga ctgcacagaa 20

<210> SEQ ID NO 8
<211> LENGTH: 20
<212> TYPE: DNA
<213> ORGANISM: Artificial Sequence
<220> FEATURE:
<223> OTHER INFORMATION: Synthetic_iNOS_Reverse

<400> SEQUENCE: 8
tgttgaaggg tgtcgtgaaa 20

<210> SEQ ID NO 9
<211> LENGTH: 20
<212> TYPE: DNA
<213> ORGANISM: Artificial Sequence
<220> FEATURE:
<223> OTHER INFORMATION: Synthetic_HO-1_Forward

<400> SEQUENCE: 9
gacagcatgt cccaggattt 20

<210> SEQ ID NO 10
<211> LENGTH: 20
<212> TYPE: DNA
<213> ORGANISM: Artificial Sequence
<220> FEATURE:
<223> OTHER INFORMATION: Synthetic_HO-1_Reverse

<400> SEQUENCE: 10
ggttctgctt gtttcgctct 20

<210> SEQ ID NO 11
<211> LENGTH: 20
<212> TYPE: DNA
<213> ORGANISM: Artificial Sequence
<220> FEATURE:
<223> OTHER INFORMATION: Synthetic_HSP70_Forward

<400> SEQUENCE: 11
gagttgagcg gcatcccgcc 20

<210> SEQ ID NO 12
<211> LENGTH: 21
<212> TYPE: DNA
<213> ORGANISM: Artificial Sequence
<220> FEATURE:
<223> OTHER INFORMATION: Synthetic_HSP70_Reverse

<400> SEQUENCE: 12
gtcctagatt cacacctgga g 21

<210> SEQ ID NO 13
<211> LENGTH: 20
<212> TYPE: DNA
<213> ORGANISM: Artificial Sequence
<220> FEATURE:
<223> OTHER INFORMATION: Synthetic_Gapdh_Forward

<400> SEQUENCE: 13
ggtgctgagt atgtcgtgga 20

<210> SEQ ID NO 14
<211> LENGTH: 20
<212> TYPE: DNA
<213> ORGANISM: Artificial Sequence
<220> FEATURE:
<223> OTHER INFORMATION: Synthetic_Gapdh_Reverse

<400> SEQUENCE: 14
ttcagctctg ggatgacctt 20

<210> SEQ ID NO 15
<211> LENGTH: 20
<212> TYPE: DNA
<213> ORGANISM: Artificial Sequence
<220> FEATURE:
<223> OTHER INFORMATION: Synthetic_IL-8_Forward

<400> SEQUENCE: 15
cactcccagc atcgtagagc 20

<210> SEQ ID NO 16
<211> LENGTH: 20
<212> TYPE: DNA
<213> ORGANISM: Artificial Sequence
<220> FEATURE:
<223> OTHER INFORMATION: Synthetic_IL-8_Reverse

<400> SEQUENCE: 16
cagtgtactt gtggcgtgga 20

<210> SEQ ID NO 17
<211> LENGTH: 20
<212> TYPE: DNA
<213> ORGANISM: Artificial Sequence
<220> FEATURE:
<223> OTHER INFORMATION: Synthetic_iNos_Forward

<400> SEQUENCE: 17
ttttcccagg caaccagacg 20

<210> SEQ ID NO 18
<211> LENGTH: 19
<212> TYPE: DNA
<213> ORGANISM: Artificial Sequence
<220> FEATURE:
<223> OTHER INFORMATION: Synthetic_iNos_Reverse

<400> SEQUENCE: 18
gtagcggggt tcagaatgg 19

<210> SEQ ID NO 19
<211> LENGTH: 20
<212> TYPE: DNA
<213> ORGANISM: Artificial Sequence
<220> FEATURE:
<223> OTHER INFORMATION: Synthetic_IFN-gamma_Forward

<400> SEQUENCE: 19
atccatgagt gctacacgcc 20

<210> SEQ ID NO 20
<211> LENGTH: 20
<212> TYPE: DNA
<213> ORGANISM: Artificial Sequence
<220> FEATURE:
<223> OTHER INFORMATION: Synthetic_IFN-gamma_Reverse

<400> SEQUENCE: 20
tctgtgggtt gttcacctcg 20

<210> SEQ ID NO 21

```
<211> LENGTH: 20
<212> TYPE: DNA
<213> ORGANISM: Artificial Sequence
<220> FEATURE:
<223> OTHER INFORMATION: Synthetic_HIF-1alpha_Forward

<400> SEQUENCE: 21

tatcactgga cttcggcagc                                                  20


<210> SEQ ID NO 22
<211> LENGTH: 20
<212> TYPE: DNA
<213> ORGANISM: Artificial Sequence
<220> FEATURE:
<223> OTHER INFORMATION: Synthetic_HIF-1alpha_Reverse

<400> SEQUENCE: 22

gctgccgaag tccagtgata                                                  20


<210> SEQ ID NO 23
<211> LENGTH: 20
<212> TYPE: DNA
<213> ORGANISM: Artificial Sequence
<220> FEATURE:
<223> OTHER INFORMATION: Synthetic_PDGF_Forward

<400> SEQUENCE: 23

aggaagccat tcccgcagtt                                                  20


<210> SEQ ID NO 24
<211> LENGTH: 20
<212> TYPE: DNA
<213> ORGANISM: Artificial Sequence
<220> FEATURE:
<223> OTHER INFORMATION: Synthetic_PDGF_Reverse

<400> SEQUENCE: 24

ctaacctcac ctggacctct                                                  20


<210> SEQ ID NO 25
<211> LENGTH: 20
<212> TYPE: DNA
<213> ORGANISM: Artificial Sequence
<220> FEATURE:
<223> OTHER INFORMATION: Synthetic_VEGF_Forward

<400> SEQUENCE: 25

caatgatgaa gccctggagt                                                  20


<210> SEQ ID NO 26
<211> LENGTH: 20
<212> TYPE: DNA
<213> ORGANISM: Artificial Sequence
<220> FEATURE:
<223> OTHER INFORMATION: Synthetic_VEGF_Reverse

<400> SEQUENCE: 26

gatttcttgc gctttcgttt                                                  20


<210> SEQ ID NO 27
<211> LENGTH: 20
<212> TYPE: DNA
<213> ORGANISM: Artificial Sequence
<220> FEATURE:
<223> OTHER INFORMATION: Synthetic_GAPDH_Forward

<400> SEQUENCE: 27
```

-continued

```
ggtgctgagt atgtcgtgga                                                   20


<210> SEQ ID NO 28
<211> LENGTH: 20
<212> TYPE: DNA
<213> ORGANISM: Artificial Sequence
<220> FEATURE:
<223> OTHER INFORMATION: Synthetic_GAPDH_Reverse

<400> SEQUENCE: 28

ttcagctctg ggatgacctt                                                   20


<210> SEQ ID NO 29
<211> LENGTH: 26
<212> TYPE: DNA
<213> ORGANISM: Artificial Sequence
<220> FEATURE:
<223> OTHER INFORMATION: Synthetic_TNF-alpha_Forward

<400> SEQUENCE: 29

ccctcacact cagatcatct tctcaa                                            26


<210> SEQ ID NO 30
<211> LENGTH: 27
<212> TYPE: DNA
<213> ORGANISM: Artificial Sequence
<220> FEATURE:
<223> OTHER INFORMATION: Synthetic_TNF-alpha_Reverse

<400> SEQUENCE: 30

tctaaggtac ttgggcaggt tgacctc                                           27
```

COMPOSITION FOR PREVENTING, TREATING, OR IMPROVING GASTROINTESTINAL DISEASES COMPRISING STRAIN OF GENUS *CORYNEBACTERIUM* AND CULTURE THEREOF

TECHNICAL FIELD

The present application relates to a composition for prevention, treatment, or improvement of a gastric disorder containing *Corynebacterium* sp. strain, its cultured product, and threonine.

BACKGROUND ART

Gastric ulcer accounts for the highest incidence of gastric lesions, and are common worldwide in all breeds. The incidence of gastric ulcer is increasing with development of the livestock industry, and together with a decrease in growth rate due to decreased appetite, efforts to prevent occurrence of gastric lesions in an animal welfare aspect are being strengthened as a symptom accompanying pains.

Threonine (Thr) is the major amino acid (AA) consisting of mucin, a protective substance for the intestinal epithelium. Mucin protein promotes protein absorption, and at the same time, protects digestive organs from strong acidic digestive fluids such as gastric juice, and plays an important role in maintaining intestinal health. It has been reported that Thr treatment in feed actually improves intestinal health by helping mucin synthesis in piglets (Non-patent literature 1).

Production of feed or food Thr is produced by a method of fermentation of microorganisms, and kinds of the microorganisms mainly used then include *Escherichia coli* (*E. coli*) and *Corynebacterium glutamicum* (*C. glutamicum*), and the like. Despite producing the same AA, these two strains are divided into gram-negative bacteria and gram-positive bacteria, respectively. The cell wall of both gram-negative bacteria and gram-positive bacteria is composed of peptidoglycan (PG). However, in case of gram-negative bacteria, in addition to PG, a lipopolysaccharide (LPS) layer consisting of lipoprotein and protein is additionally present, and as Lipid A, a somatic antigen (O antigen) is present in this LPS layer, it is toxic. Therefore, in the pharmaceutical industry, it is essential to remove endogenous toxins in parenteral drugs with harmful biological activities such as pyrogenicity, lethality, Schwartzman reactivity, adjuvant activity and macrophage activation (Non-patent literature 2).

Recently, production of amino acids for feed in a granule type by simplification (or omission) of the high purification process due to economical effectiveness of feed additives inevitably mixes bacteria used for fermentation in a heat killed form into the product. Several studies have shown that the heat killed bacteria of the representative gram-positive bacteria, lactic acid bacteria is stable to the environment with strong resistance to acid and heat, and are easy to handle as high concentration is possible, and are used as food for beneficial bacteria that have settled in the intestines, and thereby strengthen the immune enhancing activity unique to the lactic acid bacteria (Non-patent literature 3).

Against this background, the present applicants have tried to develop a pharmaceutical composition having an effect in prevention and treatment of a gastric disorder, and as a result, have confirmed that a composition comprising *Corynebacterium* sp. strain, its cultured product and threonine is effective in prevention, treatment and improvement of a gastric disorder, thereby completing the present application.

PRIOR ARTS

Non-Patent Literatures (Non-patent literature 1) Law G. (2000) Threonine requirement and the effect of threonine on gut mucin characteristics in piglets receiving intragastric nutrition. Master thesis of university of Alberta. 1-143.

(Non-patent literature 2) Miyamoto T., Okono S. and Kasai N (2009) Inactivation of *Escherichia coli* endotoxin by soft hydrothermal processing. Applied and Environmental Microbiology, 75(15), 5058-5063.

(Non-patent literature 3) Lee I. H. (2018) Latest trend surrounding animal antimicrobial agents and alternatives. Pig & Consulting, 4, 70-73.

DETAILED DESCRIPTION OF THE INVENTION

Technical Problem

The present application provides a feed composition for prevention or improvement of a gastric disorder, comprising *Corynebacterium* sp. strain, its cultured product, and threonine.

The present application provides a pharmaceutical composition for prevention or treatment of a gastric disorder, comprising *Corynebacterium* sp. strain, its cultured product, and threonine.

The present application provides a food composition for prevention or improvement of a gastric disorder, comprising *Corynebacterium* sp. strain, its cultured product, and threonine.

The present application provides an antimicrobial composition against *Helicobacter pylori*, comprising *Corynebacterium* sp. strain, its cultured product, and threonine.

Technical Solution

One aspect may provide a composition for prevention, improvement, or treatment of a gastric disorder, comprising *Corynebacterium* sp. strain, its cultured product, and threonine.

In the present application, "prevention" may mean all actions that inhibit or delay the occurrence of disease by administration of the composition according to one example, and "treatment" may mean all actions in which symptoms of suspected and onset subjects of disease are improved or beneficially changed by administration of the composition according to one example, and "improvement" may mean all actions that at least reduce parameters related to the condition in which the disease is treated, for example, the severity of symptoms, by administration of the composition according to one example. The disease may mean a gastric disorder.

One aspect may provide a feed composition for prevention or improvement of a gastric disorder, comprising *Corynebacterium* sp. strain, its cultured product, and threonine.

In the present application, "*Corynebacterium* sp. (*Coryne* sp.) strain" may comprise all *Corynebacterium* sp. strains. The *Corynebacterium* sp. strain may be for example, *Corynebacterium glutamicum, Corynebacterium ammoni-*

*agenes, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium pollutisoli, Corynebacterium imitans, Corynebacterium testudinoris*, and/or *Corynebacterium flavescens*, and more specifically, it may be *Corynebacterium glutamicum, Corynebacterium ammoniagenes*, or combination thereof (*Corynebacterium glutamicum* and *Corynebacterium ammoniagenes*).

In one example, the *Corynebacterium* sp. strain may have the productivity of threonine. In the present application, having the productivity of threonine means exhibiting the ability of producing and accumulating threonine in the microorganism and/or the medium when the corresponding microorganism is cultured in a medium.

When the composition for prevention, improvement, or treatment of a gastric disorder according to one example comprises *Corynebacterium glutamicum*, (i) an effect of prevention, improvement, or treatment of a gastric disorder and/or (ii) an anti-*Helicobacter pylori* efficacy may be excellent than a composition comprising any other kinds of *Corynebacterium* sp. strains than *Corynebacterium glutamicum* (for example, *Corynebacterium efficiens*).

When the composition for prevention, improvement, or treatment of a gastric disorder according to one example comprises *Corynebacterium ammoniagenes*, (i) an effect of prevention, improvement, or treatment of a gastric disorder and/or (ii) an anti-*Helicobacter pylori* efficacy may be excellent than a composition comprising any other kinds of *Corynebacterium* sp. strains than *Corynebacterium ammoniagenes* (for example, *Corynebacterium efficiens*).

When the composition for prevention, improvement, or treatment of a gastric disorder according to one example comprises *Corynebacterium glutamicum* and *Corynebacterium ammoniagenes*, (i) an effect of prevention, improvement, or treatment of a gastric disorder and/or (ii) an anti-*Helicobacter pylori* efficacy may be excellent than a composition comprising any other kinds of *Corynebacterium* sp. strains than *Corynebacterium glutamicum* and *Corynebacterium ammoniagenes* (for example, *Corynebacterium efficiens*).

In one example, the excellent anti-*Helicobacter pylori* efficacy of the composition may mean that the antimicrobial activity against *Helicobacter pylori* strain is excellent or the activity of preventing apoptosis of cells (for example, gastric mucosa cells) infected by *Helicobacter pylori* is excellent.

The *Corynebacterium* sp. strain may mean a concentrated microbial cell in which a culture medium is removed in the cultured solution, and it may pass through a centrifugation and/or a filtration processes to recover only the concentrated microbial cells from the cultured product.

In one example, the *Corynebacterium* sp. strain may be comprised in a heat killed bacteria form. In the present application, "heat killed bacteria" is an opposite concept of a viable bacteria, meaning a form in which growth of bacteria is prevented by heat treatment of viable bacteria and metabolites obtained through fermentation, and the like. The heat killed bacteria may comprise antimicrobial substances such as cytoplasm, cell wall, bacteriocin, and the like, polysaccharides, and/or organic acids, and the like.

The composition comprising a heat killed bacteria according to one example may have at least one characteristic selected from the group consisting of (1) to (6) as follows than the composition comprising a viable cell.

(1) Excellent acid resistance;

(2) Excellent heat resistance;

(2) Possibility of concentration at a high concentration;

(4) Excellent stability;

(5) Easy handling and storage; and (6) Possibility of being used as feed of intestinal beneficial bacteria.

The *Corynebacterium* sp. strain may be killed by Tyndall and/or heat treatment. In one example, the cultured solution sterilizing the *Corynebacterium* sp. strain and its cultured product comprise a heat killed bacteria of the strain. For example, the heat treatment may be progressed at a temperature of 60 to 130° C. for 3 to 30 minutes. In addition, the heat treatment may be progressed by ultra high temperature sterilization, autoclave, and/or hot air drying of once to 10 times. The ultra high temperature sterilization may be progressed at a temperature of 110° C. to 130° C. for 3.0 to 10.0 seconds, and for example, it may be progressed at 100° C. for 1.0 second to 10 seconds twice, and at 121° C. for 1.0 to 10.0 seconds once, and the autoclave may be performed at 120 to 125° C., or 121° C. for 10 minutes to 30 minutes, 15 minutes to 25 minutes, or 20 minutes, and the hot air drying may be performed at a temperature of 60 to 70° C.

In one specific example, it was confirmed that the composition comprising a heat killed bacteria of the *Corynebacterium* sp. strain, cultured product of *Corynebacterium* sp. strain, and threonine have the excellent (i) effect of prevention or treatment of a gastric disorder and/or (ii) anti-*Helicobacter pylori* efficacy in vitro and/or in vivo.

The composition according to one example may comprise the *Corynebacterium* sp. strain (or heat killed bacteria of the strain) in a concentration of 20 to 40 OD (wave length 560 to 565 nm), 25 to 35 OD (wave length 560 to 565 nm), or 30 OD (wave length 560 to 565 nm).

The composition according to one example may comprise 1 to 100 g/L, 5 to 100 g/L, 10 to 100 g/L, 15 to 100 g/L, 20 to 100 g/L, 21 to 100 g/L, 1 to 80 g/L, 5 to 80 g/L, 10 to 80 g/L, 15 to 80 g/L, 20 to 80 g/L, 21 to 80 g/L, 1 to 60 g/L, 5 to 60 g/L, 10 to 60 g/L, 15 to 60 g/L, 20 to 60 g/L, 21 to 60 g/L, 1 to 50 g/L, 5 to 50 g/L, 10 to 50 g/L, 15 to 50 g/L, 20 to 50 g/L, 21 to 50 g/L, 1 to 30 g/L, 5 to 30 g/L, 10 to 30 g/L, 15 to 30 g/L, 20 to 30 g/L, 21 to 30 g/L, 1 to 25 g/L, 5 to 25 g/L, 10 to 25 g/L, 15 to 25 g/L, 20 to 25 g/L, or 21 to 25 g/L of the *Corynebacterium* sp. strain (or heat killed bacteria of the strain) in a concentration of 20 to 40 OD (wave length 560 to 565 nm), 25 to 35 OD (wave length 560 to 565 nm), or 30 OD (wave length 560 to 565 nm).

The composition according to one example may comprise the *Corynebacterium* sp. strain (or heat killed bacteria of the strain) in a concentration of 1 to 100 g/L, 5 to 100 g/L, 10 to 100 g/L, 15 to 100 g/L, 20 to 100 g/L, 21 to 100 g/L, 1 to 80 g/L, 5 to 80 g/L, 10 to 80 g/L, 15 to 80 g/L, 20 to 80 g/L, 21 to 80 g/L, 1 to 60 g/L, 5 to 60 g/L, 10 to 60 g/L, 15 to 60 g/L, 20 to 60 g/L, 21 to 60 g/L, 1 to 50 g/L, 5 to 50 g/L, 10 to 50 g/L, 15 to 50 g/L, 20 to 50 g/L, 21 to 50 g/L, 1 to 30 g/L, 5 to 30 g/L, 10 to 30 g/L, 15 to 30 g/L, 20 to 30 g/L, 21 to 30 g/L, 1 to 25 g/L, 5 to 25 g/L, 10 to 25 g/L, 15 to 25 g/L, 20 to 25 g/L, or 21 to 25 g/L.

The composition according to one example may comprise the *Corynebacterium* sp. strain (or heat killed bacteria of the strain) in an amount of 0.1 to 10% by weight, 0.1 to 8% by weight, 0.1 to 5% by weight, 0.1 to 4% by weight, 0.1 to 3.5% by weight, 0.1 to 3% by weight, 0.1 to 1% by weight, 1 to 10% by weight, 1 to 8% by weight, 1 to 5% by weight, 1 to 4% by weight, 1 to 3.5% by weight, 1 to 3% by weight, 2 to 10% by weight, 2 to 8% by weight, 2 to 5% by weight, 2 to 4% by weight, 2 to 3.5% by weight, 2 to 3% by weight, 3 to 10% by weight, 3 to 8% by weight, 3 to 5% by weight, 3 to 4% by weight, 3 to 3.5% by weight, 3.5 to 10% by weight, 3.5 to 8% by weight, 3.5 to 5% by weight, or 3.5 to 4% by weight.

In one example, the *Corynebacterium* sp. strain may be comprised in the cultured product of the strain.

The "cultured product" means products obtained after culturing the *Corynebacterium* sp. strain, and may comprise fermented products. In one example, the cultured product may be fermented products that the *Corynebacterium* sp. strain is cultured in a medium. The "fermented products" mean products of enzymatic or metabolic decomposition of organic substances using a microorganism. In the present application, "fermentation" may mean all activities or processes including enzymatic or metabolic decomposition of organic substances using a microorganism, except for corruption reaction.

The cultured product (or fermented product) may be the total cultured product of the *Corynebacterium* sp. strain, its diluted solution, concentrate, dry matter, lyophilisate, lysate, and/or fraction, and the like, and the concentrate may be obtained by centrifuging or evaporating the cultured product, and the dry matter may be obtained by drying the cultured product using a drier, and the like, and the lyophilisate may be obtained by lyophilizing the cultured product using a lyophilizer, and the like, and the lysate may be obtained by physically or ultrasonically treating the strain or cultured product, and the fraction may be obtained by applying the cultured product, lysate, and the like to the method of centrifugation, chromatography, and the like.

The cultured product or fermented product may be in a solid phase (solid, for example, dry matter), a liquid phase (liquid), or a fluidized bed, but not limited thereto.

In one example, the cultured product may mean all media comprising a cultured strain, its metabolite, and/or residual nutrient, and the like, obtained by culturing the *Corynebacterium* sp. strain for a certain period.

In one example, the cultured product may mean other components except for the strain (microbial cell) and/or threonine in the fermented product in which the *Corynebacterium* sp. strain is cultured in a medium.

In one example, the cultured product may be one in which the *Corynebacterium* sp. strain is removed or is not removed.

In one example, the cultured product may be a cultured solution (or cultured product) in which the strain is removed from the cultured solution in which the *Corynebacterium* sp. strain is cultured in a medium. The cultured solution (or cultured product) in which the strain is removed may be a cell free cultured solution (or cultured product) or a cultured solution comprising a heat killed bacteria, and for example, may be a filtrate in which the strain is removed by centrifugation (centrifuged supernatant) and filtration and/or a cultured solution (or dry matter of the cultured solution) comprising a heat killed bacteria.

The composition according to one example may comprise the cultured product (or fermented product) in an amount of 1 to 80% by weight, 5 to 80% by weight, 10 to 80% by weight, 15 to 80% by weight, 20 to 80% by weight, 23 to 80% by weight, 25 to 80% by weight, 1 to 60% by weight, 5 to 60% by weight, 10 to 60% by weight, 15 to 60% by weight, 20 to 60% by weight, 23 to 60% by weight, 25 to 60% by weight, 1 to 50% by weight, 5 to 50% by weight, 10 to 50% by weight, 15 to 50% by weight, 20 to 50% by weight, 23 to 50% by weight, 25 to 50% by weight, 1 to 40% by weight, 5 to 40% by weight, 10 to 40% by weight, 15 to 40% by weight, 20 to 40% by weight, 23 to 40% by weight, 25 to 40% by weight, 1 to 30% by weight, 5 to 30% by weight, 10 to 30% by weight, 15 to 30% by weight, 20 to 30% by weight, 23 to 30% by weight, 25 to 30% by weight, 1 to 25% by weight, 5 to 25% by weight, 10 to 25% by weight, 15 to 25% by weight, 20 to 25% by weight, or 23 to 25% by weight. According to one example, the composition comprising the cultured product in the above range may have the excellent (i) effect of prevention or treatment of a gastric disorder and/or (ii) anti-*Helicobacter pylori* efficacy, than the composition comprising the cultured product with a content outside the above range.

The cultured product may comprise the *Corynebacterium* sp. strain, and may comprise the *Corynebacterium* sp. strain in the cultured product with a content of 0.1 to 10% by weight, 0.1 to 8% by weight, 0.1 to 5% by weight, 0.1 to 4% by weight, 0.1 to 3.5% by weight, 0.1 to 3% by weight, 0.1 to 1% by weight, 1 to 10% by weight, 1 to 8% by weight, 1 to 5% by weight, 1 to 4% by weight, 1 to 3.5% by weight, 1 to 3% by weight, 2 to 10% by weight, 2 to 8% by weight, 2 to 5% by weight, 2 to 4% by weight, 2 to 3.5% by weight, 2 to 3% by weight, 3 to 10% by weight, 3 to 8% by weight, 3 to 5% by weight, 3 to 4% by weight, 3 to 3.5% by weight, 3.5 to 10% by weight, 3.5 to 8% by weight, 3.5 to 5% by weight, or 3.5 to 4% by weight.

In one example, the *Corynebacterium* sp. strain and its cultured product may be a cultured product comprising a heat killed bacteria of the *Corynebacterium* sp. strain obtained by heat treatment (or sterilization (for example, autoclave or hot air drying)) the cultured product prepared by culturing the *Corynebacterium* sp. strain in a medium for a certain period.

In the present application, "culture" means a series of actions of growing and developing a microorganism under the environment condition artificially adjusted properly. The culture may use any culture condition and culture method known in the art. For example, the culture may be continuously performed in the known batch culture method, continuous culture method, fed-batch culture method, batch process or fed batch or repeated fed batch process. Then, the culture condition may be adjusted to an appropriate pH (for example, pH 5 to 9, pH 6 to 8, or pH 6.8) using a basic compound (e.g.: sodium hydroxide, potassium hydroxide, or ammonia) or an acidic compound (e.g.: phosphoric acid or sulfuric acid), but not limited thereto. In one example, bubble formation may be inhibited using an antifoaming agent such as fatty acid polyglycol ester, and/or an aerobic condition may be maintained by introducing oxygen or oxygen-containing gas mixture to the cultured product.

In one example, the culture temperature may be 20 to 45° C., 25 to 40° C., 30 to 40° C., 30 to 35° C., or 35 to 40° C., and the culture condition may be 100 to 500 rpm, 150 to 300 rpm, 150 to 250 rpm, or 200 rpm, and the culture time (period) may be 1 to 160 hours, 10 to 100 hours, 12 to 72 hours, 24 to 72 hours, 30 to 60 hours, 40 to 50 hours, 45 to 50 hours, or 48 hours. The culture period may be continued until a beneficial substance (for example, L-threonine, threonine) is obtained in a desired yield. In one example, the culture may be performed at the culture temperature in the above range for the culture time in the above range.

A medium used for culture should satisfy conditions of a specific strain in an appropriate way, and those skilled in the art may use it suitably according to the content known. According to one example, the medium for culturing the *Corynebacterium* sp. strain may refer to known literatures (for example, Manual of Methods for General Bacteriology. American Society for Bacteriology. Washington D.C., USA, 1981), but not limited thereto.

To culture the *Corynebacterium* sp. strain, survival requirements of a specific strain may be satisfied in an appropriate way by adjusting the temperature, pH, and the like, under the anaerobic condition in a common medium containing proper carbon sources, nitrogen sources, amino acids, vitamins, and the like. As the carbon source to be used in the medium, saccharide and carbohydrate (for example, glucose, sucrose, lactose, fructose, maltose, molasse, starch, and cellulose), oil and fat (for example, soybean oil, sunflower seed oil, peanut oil, and coconut oil), fatty acid (for example, palmitic acid, stearic acid, and linoleic acid), alcohol (for example, glycerol, and ethanol), and organic acid (for example, acetic acid), and the like may be separately used or used in combination, but not limited thereto. As the nitrogen source, a nitrogen-containing organic compound (e.g.: peptone, yeast extract, gravy, malt extract, corn steep liquor, soybean meal, and urea) or inorganic compound (e g ammonium sulfate, ammonium chloride, ammonium phosphate, ammonium carbonate, and ammonium nitrate), and the like may be separately used or used in combination, but not limited thereto. As the phosphate source, potassium dihydrogen phosphate, dipotassium hydrogen phosphate, nitrogen-containing salt corresponding thereto, and the like may be separately used or used in combination, but not limited thereto. In addition, the culture medium may contain other metal salts (for example, magnesium sulfate or iron sulfate) required for growth and/or comprise essential growth substances such as amino acids and vitamins, but not limited thereto.

In one example, the medium nay be a medium for producing threonine (for example, no. 435 medium), and the *Corynebacterium* sp. strain and its cultured product may be cultured product in which the *Corynebacterium* sp. strain is cultured in the medium for producing threonine, and the threonine may be released into the culture medium or be comprised in a cell.

In one example, the *Corynebacterium* sp. strain and/or its (the *Corynebacterium* sp. strain) cultured product may comprise threonine.

In one example, the *Corynebacterium* sp. strain and/or its cultured product may not comprise threonine.

In the present application, "threonine (Thr)" is a hydroxy-α-amino acid and is one of essential amino acids which are not produced in the body, meaning the amino acid having the chemical formula of $HO_2CCH(NH_2)CH(OH)CH_3$. The threonine may be an optical isomer type L (L-type threonine (L-Threonine, L-Thr)), type D, or its combination. The threonine is an essential amino acid, and consists of mucine, a protective substance for intestinal epithelium, and when it is insufficient, it may cause growth stop and weight loss.

According to one example, when the *Corynebacterium* sp. strain, its cultured product and/or threonine are mixed, the synergistically excellent (i) effect of prevention or treatment of a gastric disorder and/or (ii) anti-*Helicobacter pylori* efficacy may be shown.

The composition according to one example may comprise threonine of 50 to 90% by weight, 50 to 85% by weight, 50 to 80% by weight, 50 to 75% by weight, 50 to 70% by weight, 55 to 90% by weight, 55 to 85% by weight, 55 to 80% by weight, 55 to 75% by weight, 55 to 70% by weight, 60 to 90% by weight, 60 to 85% by weight, 60 to 80% by weight, 60 to 75% by weight, 60 to 70% by weight, 65 to 90% by weight, 65 to 85% by weight, 65 to 80% by weight, 65 to 75% by weight, 65 to 70% by weight, 70 to 90% by weight, 70 to 85% by weight, 70 to 80% by weight, 70 to 75% by weight, or 70% by weight. The composition comprising threonine in the above range may have the excellent (i) effect of prevention or treatment of a gastric disorder and/or (ii) anti-*Helicobacter pylori* efficacy than the composition comprising threonine with a content outside the above range.

The threonine may be commercially available or be produced using an extraction method, a fermentation method, an enzyme method, and/or a synthesis method, and the like. For example, it may be obtained by obtaining a fermented product comprising threonine using a Coryne-type strain and then purifying it, or be synthesized through a threonine biosynthesis pathway, and/or be chemically synthesized.

The threonine may (1) be comprised in the *Corynebacterium* sp. strain and/or its cultured product, or (2) be further comprised in a form which is not comprised in the *Corynebacterium* sp. strain and/or its cultured product, or (3) its combination (for example, the *Corynebacterium* sp. strain and its cultured product comprised in the composition comprise threonine and in addition, further comprise threonine), in the composition according to one example.

The threonine comprised in the composition according to one example may (1) be comprised in the *Corynebacterium* sp. strain, its cultured product, or both of them (strain and cultured product); or (2) be separately added; or (3) be comprised in the *Corynebacterium* sp. strain, its cultured product, or both of them (strain and cultured product) and additionally (separately) added thereto.

That the threonine is separately added may mean further adding purified threonine in addition to the threonine comprised in the strain and/or cultured product.

The threonine may be in a form of powder and/or granules. The granule-type threonine may have a particle size of 100 to 1000 μm or 200 to 1000 μm.

The composition according to one example may comprise the *Corynebacterium* sp. strain of 0.1 to 5 parts by weight, the cultured product of 10 to 90 parts by weight, and the threonine of 10 to 80 parts by weight. Specifically, the strain of 0.2 to 5 parts by weight, the cultured product of 12 to 88 parts by weight, and the threonine of 10.5 to 78 parts by weight, the strain of 0.3 to 5 parts by weight, the cultured product of 13 to 87 parts by weight, and the threonine of 11 to 77 parts by weight, the strain of 0.4 to 5 parts by weight, the cultured product of 14 to 86 parts by weight, and the threonine of 11.5 to 76 parts by weight, the strain of 0.5 to 5 parts by weight, the cultured product of 15 to 85 parts by weight, and the threonine of 12 to 75 parts by weight, the strain of 0.6 to 5 parts by weight, the cultured product of 16 to 84 parts by weight and the threonine of 12.5 to 74 parts by weight, the strain of 0.7 to 5 parts by weight, the cultured product of 17 to 83 parts by weight, and the threonine of 13 to 73 parts by weight, the strain of 0.8 to 5 parts by weight, the cultured product of 18 to 82 parts by weight, and the threonine of 13.5 to 72 parts by weight, the strain of 0.9 to 5 parts by weight, the cultured product of 19 to 81 parts by weight, and the threonine of 14 to 71 parts by weight, the strain of 0.9 to 4 parts by weight, the cultured product of 20 to 80 parts by weight, and the threonine of 14 to 70 parts by weight, the strain of 1 to 4 parts by weight, the cultured product of 21 to 79 parts by weight, and the threonine of 14 to 69 parts by weight, or the strain of 1 to 3 parts by weight, the cultured product of 22 to 78 parts by weight, and the threonine of 14 to 68 parts by weight may be comprised.

In the composition according to one example, the weight ratio of the strain and its cultured product, and threonine (weight of the strain and its cultured product: weight of threonine) may be 1:0.1 to 1:10, 1:0.1 to 1:5, 1:0.1 to 1:3, 1:0.2 to 1:10, 1:0.2 to 1:5, 1:0.2 to 1:3, 1:0.5 to 1:10, 1:0.5 to 1:5, 1:0.5 to 1:3, 1:1 to 1:10, 1:1 to 1:5, 1:1 to 1:3, 1:3 to 1:10, 1:3 to 1:5, or 1:3.

The composition according to one example may further comprise lignosulfonate. When the composition according to one example further comprises lignosulfonate, the (i) effect of prevention or treatment of a gastric disorder and/or (ii) anti-*Helicobacter pylori* efficacy may become excellent.

The composition according to one example may further comprise calcium lignosulfonate, to adjust the threonine content. According to one example, the composition may comprise calcium lignosulfonate of 0.1 to 50% by weight, 0.1 to 30% by weight, 0.1 to 25% by weight, 0.1 to 20% by weight, 0.1 to 15% by weight, 0.1 to 10% by weight, 0.1 to 7% by weight, 1 to 50% by weight, 1 to 30% by weight, 1 to 25% by weight, 1 to 20% by weight, 1 to 15% by weight, 1 to 10% by weight, 1 to 7% by weight, 3 to 50% by weight, 3 to 30% by weight, 3 to 25% by weight, 3 to 20% by weight, 3 to 15% by weight, 3 to 10% by weight, 3 to 7% by weight, 5 to 50% by weight, 5 to 30% by weight, 5 to 25% by weight, 5 to 20% by weight, 5 to 15% by weight, 5 to 10% by weight, 5 to 7% by weight, 6.5 to 50% by weight, 6.5 to 30% by weight, 6.5 to 25% by weight, 6.5 to 20% by weight, 6.5 to 15% by weight, 6.5 to 10% by weight, or 6.5 to 7% by weight. In one example, the composition may comprise the *Corynebacterium* sp. strain and its cultured product in a dried form (for example, dry matter of '*Corynebacterium* sp. strain and its cultured product'). The dry matter may be prepared by drying the *Corynebacterium* sp. strain and its cultured product, and the dry matter may comprise threonine. In one example, the drying may be performed by at least one method selected from the group consisting of vacuum drying, hot air drying, lyophilization, ambient air drying, thin film drying, and/or vacuum drying.

In one example, the composition may comprise the *Corynebacterium* sp. strain, its cultured product, and threonine in a dried form (for example, dry matter of '*Corynebacterium* sp. strain and its cultured product' comprising threonine).

The formulation of the composition according to one example may be in a form of emulsion, suspension, or solution in oil or aqueous media, or in a form of extract, powder, granule, tablet, capsule, or gel (for example, hydrogel), and may further comprise a dispersing agent or stabilizing agent.

The composition according to one specific example may be prepared by drying the *Corynebacterium* sp. strain and its cultured product (fermented product), and threonine, the *Corynebacterium* sp. strain (for example, strain in a heat killed bacteria), and a component of the cultured product other than the threonine and strain may be comprised in this composition. In one example, the composition according to one example which is prepared by drying the *Corynebacterium* sp. strain and its cultured product may be in a granule form, and this may have the excellent (i) effect of prevention or treatment of a gastric disorder and/or (ii) anti-*Helicobacter pylori* efficacy than the purified threonine in a powder form.

In the present application, "granule" means a state in which powder aggregates to form a particle 30~150 times larger, and "granulation" may mean inducing that a raw material is to be a granule by treating a process, and the like. In one example, in the process of drying the composition comprising the *Corynebacterium* sp. strain, its cultured product, and/or threonine, the composition may exhibit a granule form.

In one example, the gastric disorder may be caused by *Helicobacter pylori* infection.

In one example, the gastric disorder may be at least one selected from the group consisting of gastritis, gastric ulcer, duodenal ulcer, peptic ulcer, and gastric cancer.

The gastritis means a state in which inflammation of gastric inner wall is caused, and the gastric ulcer may occur as the balance of attack factors causing mucosa damage and defense factors protecting mucosa in the stomach and intestine is broken. The attack factors which may be considered as causes of gastric ulcer include gastric acid, various kinds of digestive enzymes, bile, taken drugs, alcohol, infection of *Helicobacter pylori*, taking non-steroidal anti-inflammatory drugs, smoking, and the like.

When the composition according to one example is used as a feed composition, a feed composition in a form in which the composition according to one example is added to a commercially available feed composition may be prepared. The feed in which the composition according to one example may be used is preferably powder or pellet formulation, or liquid formulation, but not limited thereto. In addition, the added amount of the composition of the present application which is added to the feed does not require any particular limitation.

In the present application, "feed" may mean any natural or artificial prescribed diet, meal, and the like, or a component of the meal, for animals to eat, digest or suitable therefor.

The kind of the feed is not particularly limited, and feeds commonly used in the art may be used. A non-limitative example of the feed may include plant feeds such as grains, roots, food processing by-products, algae, fiber, pharmaceutical by-products, fats and oils, starches, peels or grain by-products, or the like; and animal feeds such as proteins, inorganics, fats and oils, minerals, fats and oils, single-cell proteins, animal planktons or food, or the like. They may be used alone or in combination of two or more.

The subject (animal) to which the feed comprising the composition according to one example may be supplied is not particularly limited, but may be the mammals, fishes, crustaceans, and/or shells, and for example, may be a pig, cow, horse, goat, deer, sheep, chicken, duck, goose, turkey, dog, cat, rabbit, or fish.

The feed composition may further comprise an excipient, a diluent, or an additive. The feed composition may comprise a component effective for promoting growth of animals, a nutrient component, a nutrient supplement, a component improving the preservation stability, a coating material component, an amino acid preparation for preventing a disease, a vitamin preparation, an enzyme preparation, a non-protein nitrogen compound, a silicate preparation, a buffer, an extractant, a probiotic; enzymes such as amylase, lipase, and the like; vitamins such as L-ascorbic acid, choline chloride, inositol, and the like; minerals such as potassium chloride, iron citrate, magnesium oxide, phosphates, and the like; amino acids such as lysine, alanine, methionine, and the like; organic acids such as fumaric acid, butyric acid, lactic acid, and the like or salts thereof; anti-oxidants such as vitamin C, vitamin E, and the like, mold-inhibiting agents such as calcium propionate, and the like; emulsifiers such as lecithin, glycerin fatty acid ester, and the like; and/or pigments, and the like, in addition to the components. Although not described above, the feed composition according to one example may further comprise other nutrients within a range that may be expected by those skilled in the art.

Other aspect may provide a pharmaceutical composition for prevention or treatment of a gastric disorder, comprising *Corynebacterium* sp. strain, its cultured product, and threonine. The *Corynebacterium* sp. strain, its cultured product, threonine, and/or the gastric disorder comprised in the pharmaceutical composition for prevention or treatment according to one example are as described for the feed composition for prevention or improvement of a gastric disorder.

The pharmaceutical composition according to one example may further comprise an appropriate carrier, excipient, or diluent commonly used for preparation of pharmaceutical compositions. Specifically, the pharmaceutical composition may be used by being formulated in a form of oral formulations such as powder, granule, tablet, capsule, suspension, emulsion, syrup, aerosol, and the like, external applications, suppositories and sterilized injection solution, according to each common method. The carrier, excipient, and diluent to be comprised in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. When formulated, it is prepared using a diluent or excipient such as filler, extender, binder, wetting agent, disintegrating agent, surfactant, and the like. Solid formulations for oral administration include tablet, pill, powder, granule, capsule, and the like, and these solid formulations are prepared by mixing at least one excipient, for example, starch, calcium carbonate, sucrose or lactose, gelatin, and the like, to the composition. In addition, in addition to the simple excipient, a lubricant such as magnesium stearate and talc. Liquid formulations for oral administration include suspension, oral liquid, emulsion, syrup, and the like, and in addition to commonly used simple diluents, water and liquid paraffin, various excipients, for example, wetting agent, sweetener, air freshener, preservative, and the like may be comprised. Formulations for parenteral administration include sterilized aqueous solution, non-aqueous solvent, suspension, emulsion, freeze-dried formulation and suppositories. As the non-aqueous solvent and suspension, propylene glycol, polyethylene glycol, plant oil such as olive oil, injectable ester such as ethyl oleate, and the like may be used. As a base compound of suppositories, witepsol, Macrogol, tween 61, cacao butter, laurinum, glycerogelatin, and the like may be used.

The pharmaceutical composition according to one example may be administered in a pharmaceutically effective amount, and in the present application, "pharmaceutically effective amount" means an amount sufficient for treating or preventing disease at a reasonable benefit/risk ratio applicable for medical treatment or prevention, and the effective dose level may be determined according to factors including disease severity, drug activity, patient's age, body weight, health, gender, patient's sensitivity to drugs, administration time, administration route, and discharging rate of the composition of the present application used, treatment period, drugs used in combination or concurrently with the composition of the present application used, and other factors known in the medical field. The pharmaceutical composition according to one example may be administered as a separate therapeutic agent, or administered in combination with other therapeutic agents, and may be administered sequentially or simultaneously with a conventional therapeutic agent. In addition, it may be administered singly or multiply. It is important to administer an amount capable of obtaining the maximum effect in a minimal amount without side effects, considering all of the factors.

The dosage of the pharmaceutical composition according to one example may be about 0.0001 to 100 mg/kg, specifically, 0.001 to 10 mg/kg, to a mammal for a day. The administration frequency of the pharmaceutical composition of the present application may be administered once a day or administered several times by dividing the dosage, but not particularly limited thereto. The dosage does not limit the scope of the present application in any aspect.

The pharmaceutical composition according to one example is not limited in the administration method as long as it can reach the target tissue. For example, intra-articular injection, oral administration, intra-arterial injection, intravenous injection, or percutaneous injection, or the like is included. In addition, the pharmaceutical composition may be administered by any device capable of transporting an active substance to a target cell.

Other aspect may provide a food composition for prevention or improvement of a gastric disorder, comprising *Corynebacterium* sp. strain, its cultured product, and threonine. The *Corynebacterium* sp. strain, its cultured product, threonine, and/or the gastric disorder comprised in the food composition for prevention or improvement of a gastric disorder are as described for the feed composition for prevention or improvement of a gastric disorder.

The food includes meat, sausage, bread, chocolate, candy, snack, confectionary, pizza, ramen, other noodles, gum, dairy products including ice cream, various kinds of soup, beverage, tea, drink, alcoholic beverage, vitamin complex, health functional food and health food, and the like, and include all foods in the common meaning.

The health functional food is a term same as food for special health use (FoSHU), and means food with high medicine and medical effects, which is processed so as to effectively show the body modulating function in addition to nutrition supply. Herein, "function(al)" means obtaining a useful effect on health use, such as adjusting nutrients or physiological effects on the structure and function of the human body. The food of the present application may be prepared by a commonly used method in the art, and when prepared, it may be prepared by adding a raw material and a component commonly added. In addition, the formulation of food may be prepared without limitation as long as it is a formulated admitted as food. The composition for food of the present application may be prepared in various forms of formulations, and different from general drugs, it has an advantage of no side effects which may occur when taking drugs for a long time, and has excellent portability, and therefore, the food of the present invention may be taken as a supplement for enhancing prevention or improvement of gastric ulcer.

The health food means food having an effect of active health maintenance or enhancement compared to general food, and the health supplement food means food for health supplement purposes. In some cases, terms of health functional food, health food and health supplement food may be used interchangeably.

Specifically, the health functional food is food in which the composition according to one example is added to food materials such as beverage, tea, spice, gum, confectionary, and the like, or food prepared as capsule, powder, suspension, and the like, and means that it has a certain effect on health when ingested, but unlike general drugs, it has an advantage that there is no side effect that may occur when taking drugs for a long time using food as a raw material.

The food composition according to one example is possible to be ingested on a daily basis and therefore a high effect can be expected for prevention or improvement of a gastric disorder, and thus it may be very usefully used.

The food composition may further comprise a physiologically acceptable carrier, and the kind of the carrier is not particularly limited, and any carrier commonly used in the art may be used.

In addition, the food composition may comprise an additional component which can improve smell, taste, sight, and the like, being used commonly in the food composition. For example, vitamins A, C, D, E, B1, B2, B6, B12, niacin, biotin, folate, pantothenic acid, and the like may be comprised. Furthermore, minerals such as zinc (Zn), iron (Fe), calcium (Ca), chrome (Cr), magnesium (Mg), manganese (Mn), copper (Cu), chrome (Cr), and the like may be comprised. Moreover, amino acids such as lysine, tryptophan, cysteine, valine, and the like may be comprised.

In addition, the food composition may comprise food additives such as preservative (potassium sorbate, sodium benzoate, salicylic acid, sodium dehydroacetic acid, etc.), disinfectant (bleaching powder and higher bleaching powder, sodium hypochlorite, etc.), anti-oxidant (butylhydroxyanisole (BHA), butylhydroxytoluene (BHT), etc.), coloring agent (tar color, etc.), coloring agent (sodium nitrite, sodium nitrous acid, etc.), bleaching agent (sodium sulfite), seasoning (MSG sodium glutamate, etc.), sweetener (dulcin, cyclamate, saccharin, sodium, etc.), flavoring agent (vanillin, lactones, etc.), expansive agent (alum, potassium D-bitartrate, etc.), reinforcing agent, emulsifier, thickener (paste), coating agent, gum base, foam inhibitor, solvent, improver, and the like. The additives may be selected depending on the kind of the food and used in an appropriate amount.

The composition according to one example may be added itself or used with other food or food components, and may be suitably used according to the common method. The mixing amount of the active ingredient may be determined appropriately depending on its purpose of use (prevention, health or therapeutic treatment). In general, when preparing food or beverage, the food composition of the present application may be added in an amount of 50 parts by weight or less, specifically, 20 parts by weight or less, based on the food or beverage. However, when taking on purpose of health and hygiene for a long period, the content less than the above range may be comprised, and since there is no problem in terms of safety, the active ingredient may be used in an amount over the above range.

As one example of the food composition, it may be used as a health beverage composition, and in this case, as same as common beverage, additional components such as various flavoring agents or natural carbohydrate, or the like may be contained. The aforementioned natural carbohydrate may be monosaccharides such as glucose and fructose; disaccharides such as maltose and sucrose; polysaccharides such as dextrin and cyclodextrin; sugar-alcohols such as xylitol, sorbitol, erythritol, and the like. As the sweetener, natural sweeteners such as thaumatin and *stevia* extract; synthetic sweeteners such as saccharin and aspartame, and the like may be used. The ratio of the natural carbohydrate may be generally about 0.01 to 0.04 g, specifically, about 0.02 to 0.03 g, per 100 mL of the health beverage composition of the present application.

In addition, the health beverage composition may contain various nutrients, vitamins, electrolytes, flavoring agents, coloring agents, pectic acid, salts of pectic acid, alginate, salts of alginate, organic acids, protective colloidal thickeners, pH adjusting agents, stabilizers, preservatives, glycerin, alcohol or carbonating agents, or the like. Besides, flesh for preparation of natural fruit juice, fruit juice beverage or vegetable beverage may be contained. These components may be used independently or in combination. The ratio of these additives is not highly important, but it is common to be selected in a range of 0.01 to 0.1 part by weight per 100 parts by weight of the health beverage composition of the present application.

The food composition according to one example may be comprised in various % by weight, as long as it can exhibit an effect of prevention or improvement of a gastric disorder, but for example, the composition according to one example may be comprised in an amount of 0.00001 to 100% by weight, 0.01 to 80% by weight, or 10 to 50% by weight based on the total weight of the food composition.

The composition comprising the *Corynebacterium* sp. strain, its cultured product, and threonine according to one example may prevent, treat or improve a gastric disorder (for example, gastric ulcer), by inhibiting *Helicobacter pylori* (*H. pylori*) proliferation and inhibiting inflammation, oxidative stress, vascular growth, and/or apoptosis induced by *Helicobacter pylori.*

The composition comprising the *Corynebacterium* sp. strain, its cultured product and threonine according to one example may prevent, treat or improve a gastric disorder by promotion of mucus synthesis and release, promotion of tissue regeneration, inhibition of gastric mucosa damage, promotion of tissue regeneration, inhibition of oxidative stress, inhibition of gastric mucosa cell apoptosis, and/or inhibition of inflammation.

In the composition according to one example, it is confirmed that there is a difference in the (i) effect of prevention or treatment of a gastric disorder and/or (ii) anti-*Helicobacter pylori* efficacy, according to whether the *Corynebacterium* sp. strain is contained or not; whether the *Corynebacterium* sp. strain is comprised as a heat killed bacteria; the kind of the *Corynebacterium* sp. strain; presence or absence of the cultured product; presence or absence of threonine; and/or combination of the *Corynebacterium* sp. strain, its cultured product and threonine, and it is confirmed that the composition according to one example exhibits the most excellent.

Other aspect may provide a method for prevention, improvement, or treatment of a gastric disorder comprising administering the composition (feed composition, food composition, or pharmaceutical composition) for prevention, improvement or treatment of a gastric disorder to a subject (patient). The feed composition, food composition, pharmaceutical composition and the gastric disorder are described as above.

According to one example, the method for prevention, improvement or treatment of a gastric disorder may further comprise confirming (selecting) a subject (patient) requiring prevention, improvement or treatment of a gastric disorder, before the administering.

In the present application, "subject" may mean all animals including humans who have or are at risk of developing a gastric disorder.

The target subject to which the method for prevention or treatment of a gastric disorder is applied may be a mammal including humans who have or are at risk of developing a gastric disorder, and for example, may be a pig, cow, horse, goat, reindeer, sheep, chicken, duck, goose, turkey, dog, cat, and/or.

In the present application, "administration" means introducing the composition for prevention, improvement or treatment of a gastric disorder to a target subject by any appropriate method, and as the administration route, it may be administered through various oral or parenteral (for example, intravenous, subcutaneous, intramuscular, intraperitoneal or local application) routes which can reach the target tissue.

The method for prevention, improvement or treatment may administer the feed composition, food composition or pharmaceutical composition according to one example in a (pharmaceutically) effective dose. The appropriate total daily use amount may be determined by treatment within the correct medical determination range, and may be administered once or several times. However, the specific therapeutic effective dose for a specific subject (patient) may be differently applied according to various factors including a specific composition, subject (patient)'s age, body weight, general health condition, gender and diet, administration time, administration route and secretion rate of the composition, treatment period, and drugs to be used with the specific composition or used simultaneously, and similar factors well known in the pharmaceutical field, in addition to the kind and extent of the reaction to be achieved, and whether other agents are used in some cases.

Other aspect may provide an antimicrobial composition against *Helicobacter pylori*, comprising *Corynebacterium* sp. strain, its cultured product, and threonine. The *Corynebacterium* sp. strain, its cultured product, threonine, and/or the gastric disorder comprised in the antimicrobial composition against *Helicobacter pylori* are described for the pharmaceutical composition for prevention or treatment of a gastric disorder.

When combining the *Corynebacterium* sp. strain, its cultured product, and threonine according to one example, the antimicrobial effect against *Helicobacter pylori* may be synergistically excellent.

Other aspect may provide a composition for prevention, improvement or treatment of a gastric disorder, comprising *Corynebacterium* sp. strain, and its cultured product, and the strain and its cultured product may comprise threonine.

Other aspect may provide a composition for preparing an active ingredient for prevention, improvement or treatment of a gastric disorder comprising *Corynebacterium* sp. strain and its cultured product (fermented product), and the *Corynebacterium* sp. strain or its cultured product (fermented product) may comprise or contain threonine.

The composition for preparing an active ingredient for prevention, improvement or treatment of a gastric disorder may comprise the *Corynebacterium* sp. strain of 0.1 to 5 parts by weight, the fermented product of 10 to 90 parts by weight, and the threonine of 10 to 80 parts by weight, based on the total composition. Specifically, it may comprise the strain of 0.2 to 5 parts by weight, the fermented product of 12 to 88 parts by weight and the threonine of 10.5 to 78 parts by weight, the strain of 0.3 to 5 parts by weight, the fermented product of 13 to 87 parts by weight and the threonine of 11 to 77 parts by weight, the strain of 0.4 to 5 parts by weight, the fermented product of 14 to 86 parts by weight and the threonine of 11.5 to 76 parts by weight, the strain of 0.5 to 5 parts by weight, the fermented product of 15 to 85 parts by weight and the threonine of 12 to 75 parts by weight, the strain of 0.6 to 5 parts by weight, the fermented product of 16 to 84 parts by weight and the threonine of 12.5 to 74 parts by weight, the strain of 0.7 to 5 parts by weight, the fermented product of 17 to 83 parts by weight and the threonine of 13 to 73 parts by weight, the strain of 0.8 to 5 parts by weight, the fermented product of 18 to 82 parts by weight and the threonine of 13.5 to 72 parts by weight, the strain of 0.9 to 5 parts by weight, the fermented product of 19 to 81 parts by weight and the threonine of 14 to 71 parts by weight, the strain of 0.9 to 4 parts by weight, the fermented product of 20 to 80 parts by weight and the threonine of 14 to 70 parts by weight, the strain of 1 to 4 parts by weight, the fermented product of 21 to 79 parts by weight and the threonine of 14 to 69 parts by weight, the strain of 1 to 3 parts by weight, the fermented product of 22 to 78 parts by weight and the threonine of 14 to 68 parts by weight, based on the total composition, but not limited thereto.

The composition for preparing an active ingredient for prevention or treatment of a gastric disorder may further comprise calcium lignosulfonate, to adjust the threonine content. The calcium lignosulfonate may be comprised in an amount of 0.1 to 50% by weight, 0.1 to 30% by weight, 0.1 to 25% by weight, 0.1 to 20% by weight, 0.1 to 15% by weight, 0.1 to 10% by weight, 0.1 to 7% by weight, 1 to 50% by weight, 1 to 30% by weight, 1 to 25% by weight, 1 to 20% by weight, 1 to 15% by weight, 1 to 10% by weight, 1 to 7% by weight, 3 to 50% by weight, 3 to 30% by weight, 3 to 25% by weight, 3 to 20% by weight, 3 to 15% by weight, 3 to 10% by weight, 3 to 7% by weight, 5 to 50% by weight, 5 to 30% by weight, 5 to 25% by weight, 5 to 20% by weight, 5 to 15% by weight, 5 to 10% by weight, 5 to 7% by weight, 6.5 to 50% by weight, 6.5 to 30% by weight, 6.5 to 25% by weight, 6.5 to 20% by weight, 6.5 to 15% by weight, 6.5 to 10% by weight, 6.5 to 7% by weight, 0.1 to 18% by weight, 0.1 to 16% by weight, 0.1 to 14% by weight, 0.1 to 13% by weight, 0.1 to 12% by weight, 0.1 to 11% by weight, 0.1 to 9% by weight, 0.1 to 8% by weight, or 0.1 to 7% by weight, based on the total weight of the composition, but not limited thereto, and may be added without limitation so that the threonine in the composition reaches the desired content.

Other aspect may provide a pharmaceutical composition for prevention or treatment of a gastric disorder comprising the composition for preparing an active ingredient for prevention or treatment of a gastric disorder.

Other aspect may provide a food composition for prevention or improvement of a gastric disorder comprising the composition for preparing an active ingredient for prevention or treatment of a gastric disorder.

Other aspect may provide a feed composition for prevention or improvement of a gastric disorder comprising the composition for preparing an active ingredient for prevention or treatment of a gastric disorder.

Other aspect provides a formulation for treating a gastric disorder comprising the granular composition for preparing an active ingredient for prevention or treatment of a gastric disorder comprising the *Corynebacterium* sp. strain and its cultured product (fermented product) as an active ingredient.

The *Corynebacterium* sp. strain and its fermented product, the gastric disorder, prevention, improvement and treatment are as described above.

In the present application, "formulation" refers to processing so as to be convenient for preparation, preservation or use, and sufficiently exhibit a therapeutic effect, by mainly physical operations, for example, pulverization, mixing, kneading, leaching (brewing) or evaporation, or the like, without changing the nature of drugs, and in addition, products made thereby are also called a medicinal preparation (chemical unabridged dictionary, 2001 May 20, Sehwa editorial department).

The additives used when formulating to prepare the formulation, that is, the filler, extender, binder, wetting agent, disintegrating agent, diluent or excipient, are as described above, and the solid formulations for oral administration and additives comprised thereto, liquid formulations for oral administration and additives comprised thereto or formulations for parenteral administration and additives added thereto are as described above.

The formulation may be a solid formulation, liquid formulation and fluidized bed formulation, but not limited thereto, and any formulation exhibiting the effect of prevention, treatment and improvement of gastric ulcer may be applied without limitation.

The formulations are as described above.

Other aspect may provide a method for preparation of an active ingredient having the (1) effect of prevention, improvement or treatment of a gastric disorder; and/or (2) antimicrobial effect against *Helicobacter pylori*, comprising drying the *Corynebacterium* sp. strain and its cultured product.

The *Corynebacterium* sp. strain and its cultured product are as described above.

In one example, the drying may be performed by at least one method selected from the group consisting of vacuum drying, hot air drying, lyophilization, ambient air drying, thin film drying, and/or vacuum drying.

In one example, the drying may dry a composition in which threonine is separately added to the *Corynebacterium* sp. strain and its cultured product.

In one example, the method for preparation of an active ingredient may further comprise separately adding threonine to the dry matter prepared after the drying.

Advantageous Effects

The composition according to the present application is confirmed to be excellent in anti-*Helicobacter pylori* efficacy in the cell experiment, and efficacy of improving a gastric ulcer, efficacy of gastric mucus synthesis, and the like in the animal experiment, and therefore it may be applied as a pharmaceutical composition for prevention or treatment of a gastric disorder, or a food or feed composition for prevention or improvement of a gastric disorder.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 1 shows the antimicrobial activity against *H. pylori* of Groups 1 to 8.

FIG. 2*a* to FIG. 2*c* show the result of measuring the expression of inflammation mediators when treating Groups 1 to 8 to RGM1 cells infected with 100 MOI for 6 hours using *H. pylori* strain. Specifically, FIG. 2*a* shows the Cox-2 mRNA expression change according to the treatment of Groups 1 to 8 in the RGM1 cells infected with *H. pylori* strain, and FIG. 2*b* shows the protein expression change of iNOS according to the treatment of Groups 1 to 8 in the RGM1 cells infected with *H. pylori* strain, and FIG. 2*c* shows the phosphorylated NF-κB p65 protein expression change according to the treatment of Groups 1 to 8 in the RGM1 cells infected with *H. pylori* strain. GAPDH and β-actin are used as internal controls of mRNA and protein, respectively.

In FIG. 2*a* to FIG. 6*b*, N (first line from left) represents the negative control group (*H. pylori*-untreated RGM1 cell), and H.p (second line from left) represents the positive control group (*H. pylori*-infected RGM1 cell), and Groups 1 to 8 represent the result in the cell in which the composition of Groups 1 to 8 is treated to the *H. pylori*-infected RGM1 cell.

FIG. 3*a* shows the expression change of the oxidation stress-related protein (HIF-1a) according to the treatment of Groups 1 to 8 in the *H. pylori*-infected RGM1 cell. β-actin is used as the internal control group. FIG. 3*b* shows the result of measuring the concentration change of intracellular active oxygen according to the treatment of Groups 1 to 8 in the *H. pylori*-infected RGM1 cell (DCF increase and decrease result).

FIG. 4*a* shows the expression change of HO-1 mRNA according to the treatment of Groups 1 to 8 in the *H. pylori*-infected RGM1 cell, and FIG. 4*b* shows the GST(pi) and HO-1 protein expression change according to the treatment of Groups 1 to 8 in the *H. pylori*-infected RGM1 cell. GAPDH and β-actin are used as the internal control group.

FIG. 5 shows the apoptosis inhibitory efficacy according to the treatment of Groups 1 to 8 in the *H. pylori*-infected RGM1 cell. Specifically, FIG. 5*a* shows the expression change of Bax, and Bcl-2 protein according to the treatment of Groups 1 to 8 in the *H. pylori*-infected RGM1 cell, and β-actin is used as the internal control group. FIG. 5*b* shows the apoptosis change (TUNEL staining result) according to the treatment of Groups 1 to 8 in the *H. pylori*-infected RGM1 cell.

FIG. 6 shows the result of the change of angiogenesis and mucosal proliferation growth factors according to the treatment of Groups 1 to 8 in the *H. pylori*-infected RGM1 cell. FIG. 6*a* shows the expression change of TGF-β and VEGF protein according to the treatment of Groups 1 to 8 in the *H. pylori*-infected RGM1 cell, and β-actin is used as the internal control group. FIG. 6*b* shows the expression change of β-catenin protein according to the treatment of Groups 1 to 8 in the *H. pylori*-infected RGM1 cell, and Lamin B is used as the internal control group.

In FIG. 7*a* to FIG. 10, Groups 1~4 mean the animal experimental groups 1-4 of Table 5.

FIG. 7 shows the SRMD (stress-related mucosal disease) improvement efficacy by administration of the composition according to one example in the WIRS animal model experimental group. Specifically, FIG. 7*a* shows pathological photographs for stomach of each experimental group, and photographs in two lines on the right are indicated at ×40 magnification. FIG. 7*b* shows (A) Gross lesion index (top left graph), (B) Inflammation; pathologic score (top right graph), (C) Ulcer/erosion; pathologic score (bottom left graph), (D) Regeneration; pathologic score (bottom right graph), by administration of the composition according to one example in the WIRS animal model experimental group.

FIG. 8 shows the change of the inflammation, angiogenesis, and signaling, by administration of the composition according to one example in the WIRS animal model experimental group. (A) FIG. 8*a* shows the expression change of iNOS, TNF-α, and IFN-γ mRNA in the animal experimental groups 1-4, and FIG. 8*b* shows the expression change of PDGF mRNA in the animal experimental groups 1-4, and FIG. 8*c* shows the expression change of p-IκBα protein in the animal experimental groups 1-4, and FIG. 8*d* shows the change of P-ERK and p-JNK protein in the animal experimental groups 1-4. GAPDH and β-actin are used as the internal control group of mRNA and protein, respectively.

FIG. 9 is the result showing the change of apoptosis and cell cycle by administration of the composition according to one example in the WIRS animal model experimental group. Specifically, FIG. 9*a* is the result of TUNEL analysis showing the apoptosis level in the SRMD region of gastric mucosa in the animal experimental groups 1-4, and FIG. 9*b* shows the protein expression change of PARP-1, Bcl-2, Bax, Cleaved caspase-8, and Cleaved caspase-3, and FIG. 9*c* shows the protein expression change of CDK4 and Cyclin D1. β-actin is used as the internal control group.

FIG. 10 shows the mucin content in the stomach tissue of the animal experimental groups 1-4.

FIG. 11 shows pathological photographs of the stomach of WIRS rats in which samples comprising threonine of various % by weight are administered. The composition and content of Samples 1 to 5 of FIG. 11 are disclosed in Table 4.

DETAILED DESCRIPTION OF THE EMBODIMENTS

Hereinafter, it will be described in detail by examples to help understanding of the present application. However, the following examples illustrate the content of the present application, and the scope of the present application is not limited to the following examples. The examples of the present application are provided to more completely described the present application to those skilled in the art.

Example 1. *Corynebacterium* sp. Strain-Containing Composition and Cell Infection

Example 1-1. *Corynebacterium* sp. Strain-Containing Composition Preparation To verify the difference of the efficacy of anti-*Helicobacter pylori*, inhibition of apoptosis, and cell protection of the strain composition containing *Corynebacterium* sp. strain, and the efficacy between *Corynebacterium* sp. strains, compositions of Group 1 to Group 8 were prepared.

Wild type strains of *Corynebacterium glutamicum* (*C. glutamicum*), *Corynebacterium ammoniagenes* (*C. ammoniagenes*), and *Corynebacterium efficiens* (*C. efficiens*) were provided from CJ CheilJedang BIO R&D Center (Blossom park) and used, and the strains were inoculated to broth for producing threonine respectively, and cultured at 35° C. for 48 hours at 200 rpm. The components and contents of the broth for producing threonine are disclosed in the following Table 1.

TABLE 1

| Component | Concentration (per liter) |
|---|---|
| Glucose | 70 g |
| $KH_2PO_4$ | 1 g |
| $(NH_4)_2SO_4$ | 30 g |
| $MgSO_4 \cdot 7H_2O$ | 1 g |
| $FeSO_4 \cdot 7H_2O$ | 200 mg |
| $MnSO_4 \cdot 4H_2O$ | 100 mg |
| Biotin | 1 mg |
| Yeast extract | 2.5 g |
| Calcium-pantothenic acid | 1 mg |
| Thiamine hydrochloride | 1 mg |
| Calcium carbonate | 30 g |
| pH | 6.8 |

Group 1 comprises supernatant of fermented broth in which a microbial cell has been removed by centrifuging the fermented broth prepared by culturing *Corynebacterium glutamicum* under the above condition, and Group 2 is buffer (Tris-HCl) comprising threonine at a concentration of 100 g/L. Groups 3 to 5 were prepared by centrifuging the fermented broth prepared by culturing the strain under the above condition to collect a microbial cell, and suspending the collected microbial cell in buffer (Tris-HCl). Groups 6 to 8 are fermented broth in which each strain is cultured under the above condition, and comprise each strain and the cultured product in which each strain has been cultured in the medium (disclosed as 'supernatant of fermented broth' in Table 2). The compositions of Groups 3 to 8 comprise each strain at a concentration of 30 OD (wave length 562 nm), and comprise the strain as a heat killed bacteria through autoclave.

Groups 1 to 8 comprise threonine all, and there is a group comprising threonine in each strain (comprised in a heat killed bacteria form) or cultured product, and therefore, threonine (threonine produced through CJ BIO strains; purity >99%) were further added so that the final threonine concentration in Groups 1 to 8 was 100 g/L by measuring the threonine content in the strain and/or cultured product.

The components of each group were disclosed in the following Table 2. In Table 2, 'supernatant of fermented broth' of Group 1 and Group 6 means that a microbial cell is removed in the cultured product prepared by culturing '*C. glutamicum* strain' under the above condition, and the supernatant of fermented broth of Groups 7 and 8 means that a microbial cell is removed in the cultured product prepared by culturing '*C. ammoniagenes* strain' and '*C. efficiens* strain' under the above condition.

TABLE 2

| Group | Components in compositions |
|---|---|
| Group 1 | Threonine + Supernatant of fermented broth |
| Group 2 | Threonine |
| Group 3 | Threonine + *C. glutamicum* |
| Group 4 | Threonine + *C. ammoniagenes* |
| Group 5 | Threonine + *C. efficiens* |
| Group 6 | Threonine + *C. glutamicum* + Supernatant of fermented broth |
| Group 7 | Threonine + *C. ammoniagenes* + Supernatant of fermented broth |
| Group 8 | Threonine + *C. efficiens* + Supernatant of fermented broth |

Groups 1-8 disclosed in the following Examples 2 to 7 and FIG. 1 to FIG. 6*b* mean the Groups 1-8 of Table 2.

Example 1-2. Rat Gastric Mucosa Cell Line Culturing

The gastric mucosa cell line of a normal rat, RGM1 cell was cultured in Ham F12 mixed medium and DMEM (Dulbecco's modified essential medium) comprising 10% fetal bovine serum with a 37° C. cell incubator (95% air, 5% $CO_2$). The RGM1 cell line was established by Professor Matsui of Japan Tsukuba University, and used after consent.

Example 1-3. *H. pylori* Strain and Cell Infection

*Helicobacter pylori* (*H. pylori*) strain (cytotoxin-associated gene A [CagA]+strain, NCTC 11637) was purchased from ATCC (American Type Culture Collection, Rockville, MD). The *H. pylori* strain was cultured with shaking under the condition of 10% $CO_2$ until it was $1\times10^8$ CFU/ml (OD 600=1) in *Brucella* broth in which 5% bovine calf serum and an antibiotic were added.

The RGM1 cell was infected with the *H. pylori* strain for 6 hours at the multiplicity of infection (MOI) of 100:1 (hereinafter, 100 MOI).

Example 2. Test of Anti-*Helicobacter* Efficacy of the Composition Containing *Corynebacterium* sp. Strain In Vitro The growth inhibitory efficacy of *H. pylori*, that is anti-*Helicobacter* efficacy, was measured in a blood agar plate using disc diffusion assay. Specifically, TSA (Trypticase™ Soy Agar) 40 g/L was dissolved in purified water and then autoclaved (121° C., 20 min). After cooling to about 50° C., 5% sheep blood was added, and then an antibiotic {trimethoprim (5 mg/L), polymyxin B (2500 U/L), vancomycin (10 mg/L)} was added. The medium was aliquoted by 20 to 25 ml, in the sterilized plate, and then was stored at 4° C.

*H. pylori* strain solution 200 μl was aliquoted and spreaded on the prepared blood agar plate, and 40 μl of each composition of Groups 1 to 8 prepared in Example 1-1 was absorbed to each disc paper, and was cultured in a $CO_2$ incubator of 37° C. for 48 hours, and then the diameter of the clear zone around the disc was measured and shown in FIG. 1 (the result of Group 1 was not represented in the graph). In FIG. 1, 'Non-treated' means the RGM1 cell uninfected by *H. pylori*.

As shown in FIG. 1, it was confirmed that Groups 6 and 7 had the significant anti-*Helicobacter* activity, as the numerical value of the diameter of the clear zone was significantly high in Groups 6 and 7 compared to the untreated group.

In addition, the appropriate concentration of Groups 1-8 to be used in the following experiments was to be derived.

The diluted solutions in which the compositions of Groups 1 to 8 prepared in Example 1-1 were diluted by ¼, 1/40, or 1/100 were treated to *H. pylori* by 40 μl, respectively, and the cell viability was measured. As at the dilution concentration of ¼, the viability of 0.5 or less was shown in many groups, and at the dilution concentration of 1/100, there was no clear result difference between groups, the diluted solution of 1/40 in which the significant result difference was shown compared to Group 1 was used in the following experiments.

Example 3. Test of Change of Inflammation Mediator and NF-κB Transcribing the Same by the Composition Containing *Corynebacterium* sp. Strain As the method of Example 1-3, the RGM1 cell infected by *H. pylori* (100 MOI) was treated with the compositions of Groups 1 to 8, diluted by 1/40, of 40 μl, respectively for 6 hours. Then, in the RGM1 cell in which the compositions were treated, the expression level of the inflammation mediator, Cox-2 mRNA was confirmed through RT-PCT (Reverse transcription PCR) analysis, and the result was shown in FIG. 2*a*.

Specifically, RNA was extracted using TRIzol (Gibco BRL, Rockville, MD), and the extracted RNA was synthesized into cDNA using moloney murine leukemia virus reverse transcriptase (Perkin Elmer, Morrisville, NC). The nucleic sequence of each primer used for PCR analysis was shown in the following Table 3, and as an internal standard, glyceraldehyde 3-phosphate dehydrogenase (GAPDH) was used.

TABLE 3

| Gene | Forward Primer(5'→3') | Reverse Primer(5'→3') |
|---|---|---|
| IL-1β | CAG GCT CCG AGA TGA ACA ACA AA(SEQ ID NO: 1) | TGG GGA ACT CTG CAG ACT CA(SEQ ID NO: 2) |
| IL-8 | CAG ACA GTG GCA GGG ATT CA(SEQ ID NO: 3) | TTG GGG ACA CCC TTT AGC AT(SEQ ID NO: 4) |
| Cox-2 | GAA ATG GCT GCA GAG TTG AA(SEQ ID NO: 5) | TCA TCT AGT CTG GAG TGG GA(SEQ ID NO: 6) |
| iNOS | CTC ACT GGG ACT GCA CAG AA(SEQ ID NO: 7) | TGT TGA AGG GTG TCG TGA AA(SEQ ID NO: 8) |
| HO-1 | GAC AGC ATG TCC CAG GAT TT(SEQ ID NO: 9) | GGT TCT GCT TGT TTC GCTC T(SEQ ID NO: 10) |
| HSP70 | GAG TTG AGC GGC ATC CCG CC(SEQIDNO: 11) | GTC CTA GAT TCA GAG(SEQ ID NO: 12) |
| Gapdh | GGT GCT GAG TAT GTC GTG GA(SEQ ID NO: 13) | TTC AGC TCT GGG ATG ACC TT(SEQ ID NO: 14) |

In addition, in the RGM1 cell in which the compositions were treated, the increase and decrease of the expression level of iNOS protein and NF-κB p65 phosphorylation transcribing it was confirmed through western blot analysis, and the result was shown in FIG. 2*b* and FIG. 2*c*.

Specifically, the cell cultured by treating the compositions was washed with PBS (phosphate buffered saline) solution, and then was dissolved with cell lysis buffer (150 mM NaCl, 0.5% Triton X-100, 50 mM tris-HCl, pH 7.4, 25 mM NaF, 20 mM ethyleneglycol-bis(βN'-tetraacetic acid, 1 mM dithiothreitol, 1 mM $Na_3VO_4$, Protease Inhibitor Cocktail tablet [Boehringer, Manneim, Germany]) to make protein lysate. After electrophoresis of them by SDS-PAGE (sodium dodecyl sulfate-polyacrylamide gel electrophoresis), unfolded protein was transferred to PVDF membrane (Gelman Sciences, Ann Arbor, MI) to react it with a primary antibody and a secondary antibody, respectively, and then it was analyzed using a chemoluminescence system.

As shown in FIG. 2*a*, compared to the normal RGM1 cell (N), in the RGM1 cell infected by *H. pylori* (H.p), Cox-2 mRNA was significantly increased, and the increased mRNA expression of Cox-2 by *H. pylori* infection was most significantly reduced by addition of the composition of Group 6.

As shown in FIG. 2*b* and FIG. 2*c*, the iNOS protein expression and phosphorylation of NF-κB p65 transcribing it was significantly increased by *H. pylori* infection, but the iNOS protein expression and phosphorylation of NF-κB p65 transcribing it was most significantly decreased by addition of the composition of Group 6. From the result, it could be seen that the composition according to one example regulated the inflammation mediating pathway by the *Helicobacter* strain.

Example 4. Test of Efficacy of Weakening Oxidative Stress by the Composition Containing *Corynebacterium* sp. Strain In Vitro As the method of Example 1-3, the RGM1 cell infected by *H. pylori* (100 MOI) was treated with the compositions of Groups 1 to 8, diluted by 1/40, of 40 μl, respectively for 6 hours. Then, western blot was performed by the similar method to Example 3, and the expression level change of oxidative stress-associated HIF-1α was measured, and the result was shown in FIG. 3*a*.

As shown in FIG. 3*a*, HIF-1a was significantly increased by *Helicobacter pylori* infection, and the HIF-1a expression was significantly reduced in Groups 6 and 7.

In addition, to measure the concentration change of intracellular reactive oxygen, DCF enhancement reaction utilizing a DCF-DA probe was analyzed with a confocal imager. A non-fluorescent substance, DCF-DA (2',7'-dichlorofluorescein diacetate) is oxidized by reactive oxygen species (ROS) when peroxides are present in a cell and exhibits green fluorescence, and therefore the amount of reactive oxygen species may be directly quantified by the fluorescence intensity at a specific wavelength. Specifically, the RGM-1 cell (*H. pylori* untreated RGM1 cell; or RGM1 cell infected by *H. pylori* (100 MOI) (Example 1-3)) of $5\times10^5$ cells/well was aliquoted to a 24 well plate, and was cultured in a 37° C. incubator (95% air, 5% $CO_2$) overnight, and then the compositions of Groups 1 to 8 were treated for a certain time, respectively. The cell was washed with DMEM, and then 10 μg/ml DCF-DA (2',7'-dichlorofluorescein diacetate, Sigma-Aldrich Co., St Louis, MO) was added to the medium and it was incubated in an incubator for 30 minutes. After incubation, the cell washed with PBS of 4° C. was observed and photographed with a fluorescence microscope, and the result was shown in FIG. 3*b*.

As shown in FIG. 3*b*, it was confirmed that the fluorescence intensity of DCF-DA increased after *Helicobacter pylori* infection was statistically significantly reduced in Groups 1, 3, 6 and 8 treated groups ($P<0.05$), and in the Group 6 treated group, the reduction degree was the largest ($P<0.01$). From the result, it could be seen that the composition according to one example could immediately cope with oxidative stress or hypoxia response by *Helicobacter pylori* strain.

Example 5. Test of *Helicobacter pylori*-Associated Anti-Oxidation-Mediated Cell Protection Efficacy by the Composition Containing *Corynebacterium* sp. Strain In Vitro As the method of Example 1-3, the RGM1 cell infected by *H. pylori* (100 MOI) was treated with the compositions of Groups 1 to 8, diluted by 1/40, of 40 μl, respectively for 6 hours. Then, the mRNA expression change of HO-1 of the anti-oxidation function, a representative cytoprotective factor, was analyzed by the method according to Example 3 (PCR), and was shown in FIG. 4*a*, and the HO-1 and GST (glutathione-s-transferase(pi)) protein expression change was analyzed similarly to the method according to Example 3 (western blot analysis) and was shown in FIG. 4*b*.

As a result, as FIG. 4*a* and FIG. 4*b*, in the control group, the significant reduction of HO-1 mRNA and protein was observed after *Helicobacter pylori* infection, and in the Groups 6 to 8 treated groups, the reduced HO-1 expression was significantly increased, and among them, in the Group 6 treated group, the HO-1 expression was most significantly increased. In addition, as shown in FIG. 4*b*, in Groups 6 and 7, the GST(pi) expression was significantly reduced, and among them, in the Group 6 treated group, the GST(pi) expression was most significantly reduced.

From the result, it could be seen that the composition according to one example exhibited the anti-oxidation action and cell protection efficacy mostly based on the HO-1 reaction for *Helicobacter pylori* strain.

Example 6. Test of *Helicobacter pylori*-Associated Apoptosis Inhibitory Efficacy by the Composition Containing *Corynebacterium* sp. Strain In Vitro As the method of Example 1-3, the RGM1 cell infected by *H. pylori* (100 MOI) was treated with the compositions of Groups 1 to 8, diluted by 1/40, of 40 μl, respectively for 6 hours. Then, by the method similar to Example 3, the expression of Bcl-2 and Bax was confirmed by western blot, and the result was shown in FIG. 5*a*, and apoptosis was analyzed by TUNEL staining, and the result was shown in FIG. 5*b*. Specifically, TUNEL staining was conducted by aliquoting the cell to Lab-Tek chamber slide by $1\times10^5$ cells/chamber and then culturing in a 37° C. incubator (95% air, 5% $CO_2$). Then, after treating each reagent for a certain time, it was performed by the manufacturer's experimental method using an apoptosis detection kit (Oncogene Research Products, Cambridge, MA). The cultured solution was removed and washed with PBS solution 3 times, and then 4% PFA (paraformaldehyde) was added and it was fixed at a room temperature for 20 minutes. After washing with PBS twice again, 0.1% Triton X-100 was treated at 4° C. for 5 minutes, and light was blocked and then it was reacted with solution made by mixing TdT (terminal deoxynucleotidyl transferase) and nucleotide mixture at 37° C. for 60 minutes. After washing with PBS, apoptosis was observed with a fluorescence microscope.

As shown in FIG. 5*a*, the decrease of expression of Bcl-2 and increase of expression of Bax could be observed in the cell infected by *H. pylori* (H.p), and it could be confirmed that the Bax expression significantly increased was decreased and the decreased Bcl-2 expression was increased in the Groups 6 to 8 treated groups, and among them, in the Group 6 treated group, the effect was most excellent.

*Helicobacter pylori* infection is known to induce mucosa damage and ulcer by significant increase of apoptosis, and as shown in FIG. 5*b*, in the result of TUNEL staining, the statistically significant increase of apoptosis was observed by *Helicobacter pylori* infection ($P<0.01$), but in the Groups 6 to 8 treated groups, apoptosis was significantly reduced, and among them, in the Group 6 treated group, apoptosis was reduced mostly.

Example 7. Test of Change of *Helicobacter pylori*-Associated Cell Growth, Vascular Growth, and Proliferation Factor by the Composition Containing *Corynebacterium* sp. Strain In Vitro As the method of Example 1-3, the RGM1 cell infected by *H. pylori* (100 MOI) was treated with the compositions of Groups 1 to 8, diluted by 1/40, of 40 μl, respectively for 6 hours. Then, by the method similar to Example 3, the change of TGF-β and VEGF was analyzed by western blot, and the result was shown in FIG. 6*a*.

As a result, as shown in FIG. 6*a*, TGF-β and VEGF increased by *Helicobacter pylori* infection promoted indiscriminate mucosa proliferation or cancerous inflammation, but in the Groups 6 to 8 treated groups, the expression of TGF-β and VEGF was significantly reduced, and in particular, in the Group 6 treated group, the expression of TGF-β and VEGF was reduced mostly. From this, the result that the composition according to one example could alleviate all inflammation or canceration by *Helicobacter pylori* infection was shown.

In addition, nuclear transfer of β-catenin was confirmed utilizing nuclear fraction in the *Helicobacter pylori*-infected cell by western blot, and the result was shown in FIG. 6*b*. As shown in FIG. 6*b*, it was confirmed that the nuclear transfer of β-catenin increased by *Helicobacter pylori* infection could be significantly inhibited by treatment of the Group 6.

All the experimental values of Examples 1 to 7 were statistically verified by the method through T-test, and $p<0.05$ or more was defined as statistically significant.

Example 8. Preparation of Sample Comprising Threonine fermented broth prepared by inoculating *C. glutamicum* wild type strain (CJ CheilJedang BIO R&D Center (Blossom park)) to broth for producing threonine (Table 1) and culturing it under the condition of 35° C. and 200 rpm for 48 hours was purified and crystallized to prepare Sample 1. Sample 1 comprised 99% by weight or more of purified threonine in a powder form.

fermented broth (comprising *C. glutamicum*) obtained by culturing *C. glutamicum* in a medium for producing threonine was directly dried (hot air drying at 60 to 70° C.) to prepare Sample 2. In addition, calcium lignosulfonate (Aladdin industrial Co., Shanghai, Chana) was added to fermented broth obtained by culturing *C. glutamicum* under the above condition in various contents, and the fermented broth (comprising *C. glutamicum*) in which calcium lignosulfonate was added was dried (hot air drying at 60 to 70° C.) to prepare Samples 3 to 5. Samples 2 to 5 comprised *C. glutamicum* in a form of a heat killed bacteria through hot air drying.

Samples 2 to 5 were prepared in a granule form having a particle size of about 200 to 1000 μm. The components and contents of Samples 1 to 5 were disclosed in Table 4. In Table 4, Thr (% by weight), calcium lignosulfonate (% by weight), and other components of the fermented product (comprising *C. glutamicum* microbial cell) (% by weight) mean % by weight in the dry matter prepared by drying the fermented broth, and the fermented product in the dry matter comprises *C. glutamicum* strain. In addition, the content of *C. glutamicum* strain comprised in the fermented product was disclosed in Table 4.

TABLE 4

| | Thr (% by weight) | Fermented product (% by weight) | *C. glutamicum* in the fermented product (% by weight)[1] | Calcium lignosulfonate (% by weight) |
|---|---|---|---|---|
| Sample 1 | 100.0 | — | — | — |
| Sample 2 | 75 | 25.0 | 4.0 | 0.0 |
| Sample 3 | 70 | 23.3 | 3.8 | 6.7 |

TABLE 4-continued

| | Thr (% by weight) | Fermented product (% by weight) | *C. glutamicum* in the fermented product (% by weight)[1] | Calcium lignosulfonate (% by weight) |
|---|---|---|---|---|
| Sample 4 | 65 | 21.7 | 3.5 | 13.3 |
| Sample 5 | 60 | 20.0 | 3.2 | 20.0 |

[1]value converted when the content of the microbial cell in the fermented product is dried Example 9. WIRS (Water Immersion-Restraint Stress) Model Preparation for SRMD (Stress-Related Mucosal Disease)

110 SD rats in total were purchased from Charles River (Osaka, Japan) and stored in an animal facility. The experimental animals were handled in the authorized animal facility according to AAALAC International Animal Care Policies. The animals were fasted 24 hours prior to be exposed to WIRS, and water was freely available. 10 rats of each group were placed in a cage for WIRS and immersed in water for 6 hours.

Sample 1 to Sample 5 prepared in Example 8 were orally administered to rats 8 hours before WIRS treatment, so that the same amount of threonine was administered (0.15% by weight/diet), and after applying WIRS for 6 hours, the animals were sacrificed and the stomach was extracted and incised and contents were removed, and a picture of the inner surface of the stomach was taken and this was shown in FIG. 11. As shown in FIG. 11, as the result of observing the stomach tissue of rats by naked eyes, it could be confirmed that in the WIRS induced group (the second row in FIG. 11), gastrorrhagia was caused, and the degree of gastrorrhagia was reduced (excellent therapeutic effect of gastric ulcer) in order of Sample 1<Sample 5<Sample 4<Sample 3 or Sample 2.

On the other hand, the following experiment was conducted by dividing into 4 animal experimental groups as indicated in the following Table 5. They were divided into a untreated group in which nothing was treated after oral administration of saline solution (positive control group, animal experimental group 1), WIRS Group in which WIRS was applied for 6 hours (negative control group, animal experimental group 2), and animal experimental groups in which feed containing Sample 1 (prepared in Example 8) of 0.15% by weight (animal experimental group 3) and feed containing Sample 3 (prepared in Example 8) of 0.21% by weight (animal experimental group 4) were orally treated by 30 mg/kg body, respectively, 8 hours before WIRS treatment. The content of L-Thr (L-threonine) in the feed of the animal experimental groups 3 and 4 was set to 0.15% by weight/diet equally.

TABLE 5

| Animal experimental group | Experimental animal | WIRS induction | Test substance (supplied 8 hours before WIRS treatment) | Administration dose (% by weight/diet) | Number of animals |
|---|---|---|---|---|---|
| 1 | Rat | No | Positive control group (No-stress, No-Thr) | 0 | 10 |
| 2 | | WIRS | Negative control group (No-Thr) | 0 | 20 |
| 3 | | induction | Sample 1 (Example 8; L-Thr) | 0.15 | 10 |
| 4 | | for 6 hours | Sample 3 (Example 8; L-Thr + *C. glutamicum* fermented product (comprising a microbial cell)) | 0.21 | 10 |

All experimental animals (rat) were sacrificed with a high dose of anesthetic (thiopental sodium, 50 mg/kg) after 6 hours of WIRS. The animal experimental groups 1-4 disclosed in the following Examples 10 to 12 mean the animal experimental groups 1-4 of the Table 5, and in FIG. 7*a* to FIG. 10, Groups 1-4 mean the animal experimental groups 1-4 of Table 5.

Example 10. Test of SRMD (Stress-Related Mucosal Disease) Improving Efficacy

The stomach of the rat sacrificed in Example 9 was incised and opened along the larger curvature, and then washed with cold PBS solution. After determining the number and size of erosions or ulcers by enlarged photographs, the half was anatomized for anatomical observation. The incised stomach was spread over plastic sheet and fixed in 10% buffer formalin for 4 hours and used for production of a paraffin tissue slide, and the other half was stored in a liquid nitrogen tank for molecular biological observation. In addition, the mucosal homogenate was stored by mixing the same animal experimental groups.

The stomach sample was observed using a microscope by naked eyes (FIG. 7*a*), and in the control group and each experimental group (animal experimental groups 1-4), gross lesion index, inflammation; pathologic score, ulcer/erosion; pathologic score, regeneration; pathologic score were calculated and shown in FIG. 7*b*. As shown in FIG. 7*a*, significant occurrence of SRMD such as erosions, hemorrhage, and ulcers was shown in all rats of the animal experimental group 2, but SRMD was significantly improved in the animal experimental group 3 and animal experimental group 4. As shown in FIG. 7*b*, gross lesion index, inflammation; pathologic score, ulcer/erosion; pathologic score, regeneration; pathologic score were significantly ($p<0.05$) improved in the animal experimental groups 3 and 4, and in particular, the gross lesion index of the animal experimental group 4 was significantly lower than the animal experimental group 3, and the regeneration; pathologic score was significantly improved than the animal experimental group 3.

Example 11. Test of Anti-Inflammatory Efficacy

Since SRMD was physiologically related to ischemic-reperfusion damage, in the animal experimental groups 1 to 4, mRNA expression of angiogenesis growth factors including PDGF (platelet-derived growth factor) and mRNA expression of inflammation mediators, iNOS, TNF-α, IFN-γ, and PDGF were measured, and the result was shown in FIG. 8*a* and FIG. 8*b*.

Specifically, the total RNA was extracted using RNeasy Mini kit (Qiagen Korea, Seoul, Korea). Primers used for measuring the expression of inflammatory cytokines and mediators were shown in the following Table 6. Amplification was analyzed using 10× reaction buffer (Promega Korea, Seoul, Korea), 1.5 mM/L $MgCl_2$, 200 mM/L deoxynucleotide triphosphate (dNTP), each primer 1 mM/L, and Taq DNA polymerase (Promega) 2.5 unit, using Perkin-Elmer GeneAmp PCR System 2400. Each cycle was composed of denaturation at 95° C. for 1 minute, annealing at 55° C. for 45 minutes, and amplification at 72° C. for 45 seconds.

TABLE 6

| Gene | Forward Primer(5'→3') | Reverse Primer(5'→3') |
|---|---|---|
| IL-8 | CACTCCCAGCATCGTAGAGC (SEQ ID NO: 15) | CAGTGTACTTGTGGCGTGGA (SEQ ID NO: 16) |
| iNos | TTTTCCCAGGCAACCAGACG (SEQ ID NO: 17) | GTAGCGGGGTTCAGAATGG (SEQ ID NO: 18) |
| IFN-γ | ATCCATGAGTGCTACACGCC (SEQ ID NO: 19) | TCTGTGGGTTGTTCACCTCG (SEQ ID NO: 20) |
| HIF-1α | TATCACTGGACTTCGGCAGC (SEQ ID NO: 21) | GCTGCCGAAGTCCAGTGATA (SEQ ID NO: 22) |
| PDGF | AGGAAGCCATTCCCGCAGTT (SEQ ID NO: 23) | CTAACCTCACCTGGACCTCT (SEQ ID NO: 24) |
| VEGF | CAATGATGAAGCCCTGGAGT (SEQ ID NO: 25) | GATTTCTTGCGCTTTCGTTT (SEQ ID NO: 26) |
| TNF-α | CCCTCACACTCAGATCATCT TCTCAA(SEQ ID NO: 29) | TCTAAGGTACTTGGGCAGGTT GACCTC(SEQ ID NO: 30) |
| GAPDH | GGTGCTGAGTATGTCGTGGA (SEQ ID NO: 27) | TTCAGCTCTGGGATGACCTT (SEQ ID NO: 28) |

In addition, in each of the animal experimental groups 1-4, the protein level of p-IκBα, p-ERK, and p-JNK was measured and shown in FIG. 8*c* and FIG. 8*d*. Specifically, to perform western blot for measuring the protein level, the collected gastric mucosa was homogenized in ice-cold 20 mM Tris-HCl buffer (pH 7.5) containing 2 mM EDTA (ethylenediaminetetraacetic acid), 0.5 mM EGTA (ethylene glycol tetraacetic acid), 300 mM sucrose, and 2 mM PMSF (phenylmethylsulfonyl fluoride) with a tissue homogenator. After electrophoresis of protein of 30 μg in 8% SDS-PAGE (sodium dodecyl sulfate-polyacrylamide gel electrophoresis) gel, it was transferred to PVDF (polyvinylidene fluoride) membrane using a semidry transfer system (Hoefer, Holliston, MA, USA). Non-specific binding was blocked by incubation with 5% non-fat dry milk. The membrane was thermostatically incubated with a 500-fold diluted solution of a primary antibody at 4° C. overnight, and then incubated with an HRP (horseradish peroxidase) binding-secondary antibody diluted by 1:1000. The immune complex was detected using ECL detection kit (Amersham Biosciences Korea, Seoul, Korea) and X-ray film was automatically irradiated. Antibodies used for western blot were as follows. β-actin, iNOS (nitric oxide synthase), COX-2 (cyclooxygenase), P-JNK (phosphor-JNK), P-ERK (phosphor-ERK), Bcl-2 (B-cell lymphoma 2), Bax (B-cell lymphoma-2-associated X-protein), and cyclin D1 antibodies were purchased from Santa Cruz Biotechnology (Santa Cruz, CA). p-IκBα (phosphorylated inhibitor of kappa B alpha), p-STAT3 (phosphorylated signal transducer and activator of transcription 3), PARP (poly(ADP-ribose) polymerase), CDK4 (cyclin-dependent kinase 4), and CDK2 (cyclin dependent kinase 2) were purchased from Cell Signaling Technology (Beverly, MA). HO-1 (A heme oxygenase-1) antibody was purchased from Enzo life Sciences (Farmingdale, NY).

As shown in FIG. 8*a*, in the animal experimental group 2 (WIRD induced SRMD), mRNA expression of iNOS, TNF-α, and interferon gamma (IFN-γ) was significantly increased, but the increased expression of the inflammation mediators (iNOS, TNF-α, IFN-γ) was significantly reduced in the animal experimental group 3 or animal experimental group 4 ($P<0.01$ or $P<0.05$, FIG. 8*a*), and the expression of TNF-α and iFN-γ was significantly reduced particularly in the animal experimental group 4 than the animal experimental group 3 (P<0.05, FIG. 8*a*).

As shown in FIG. 8*b*, the expression of the angiogenesis growth factor, PDGF was significantly increased in the animal experimental group 2, but it was significantly reduced in the animal experimental group 3 or animal experimental group 4 (P<0.01, FIG. 8*b*), and in particular, in the animal experimental group 4, the level of reduction was higher.

As shown in FIG. 8*c*, as the result of measuring the expression of p-IκBα at the protein level, the expression of p-IκBα was significantly reduced by WIRS in the animal experimental group 2, and the reduction of the p-IκBα expression was related to transcriptional activation of NF-κB. Meanwhile, the expression of p-IκBα reduced was significantly increased (P<0.01, FIG. 8*c*), and the expression of p-IκBα was significantly increased than the animal experimental group 3 (P<0.01, FIG. 8*c*) in the animal experimental group 4, and the increase of the expression of p-IκBα induced redox inhibition of NF-κB.

On the other hand, regarding signaling related to ischemia and inflammation, as shown in FIG. 8*d*, in the animal experimental group 2, p-ERK and p-JNK activation was shown, and in the animal experimental group 4, the signaling was inactivated all, but in the animal experimental group 3, it was partially inactivated (P<0.01).

Example 12. Test of Gastric Mucosa Protection Efficacy

Since SRMD causing erosions or ulcers showed apoptosis increased in the corresponding region, apoptosis on the gastric mucosa was measured according to the animal experimental group. Specifically, apoptosis was visualized using TdT FragEL DNA fragmentation detection kit (Oncogene Research Products, Cambridge, MA) and TUNEL (Terminal deoxynucleotidyl transferase-mediated nick end labeling) method. To measure AI (apoptotic index) by finding a region in which apoptosis occurs in a large quantity (apoptotic hot spot) in each experimental group, TUNEL-immunostained section (terminal deoxynucleotidyl transferase mediated dUTP nick-end labeling (TUNEL)-immunostained section) was enlarged 100 folds and scanned. Then, the number of TUNEL-positive cells was counted in 400 fields to record AI. The mean coefficient was determined by selection at least 5 hot spots randomly in fragments including corrosive or ulcer lesions, and the result was shown in FIG. 9*a*, and the result was indicated by the mean percentage of the total cell number. As shown in FIG. 9*a*, apoptosis was significantly increased in the animal experimental group 2 than the animal experimental group 1, and the increased apoptosis level was significantly reduced in the animal experimental group 3 and animal experimental group 4 than the animal experimental group 2 (P<0.01, FIG. 9*a*), and it was observed at a significantly lower level in the animal experimental group 4 than the animal experimental group 3 (P<0.01, FIG. 9*a*).

To verify the TUNEL result, for the expression of Bcl-2, apoptosis-preventing protein, and cleaved PARP, Bax, cleaved caspase-8, and cleaved caspase-3 inducing apoptosis, the western blot analysis was performed by the method of Example 11, and the result was shown in FIG. 9*b*.

As shown in FIG. 9*b*, PARP division, Bax, cleaved caspase-8, and cleaved caspase-3 expression were significantly increased in the animal experimental group 2, and the increased PARP division, Bax, cleaved caspase-8, and cleaved caspase-3 expression were significantly reduced in the animal experimental groups 3 and 4, and they were observed at a significantly lower level particularly in the animal experimental group 4 than the animal experimental group 3. On the other hand, the expression of Bcl-2, the apoptosis-preventing protein, was significantly increased in the animal experimental group 4 (FIG. 9*b*).

The activity of CDK4 and Cyclin D1, cell cycle-related genes, was confirmed at a protein level by the method according to Example 11, and the result was shown in FIG. 9*c*. As shown in FIG. 9*c*, the expression of CDK4 and Cyclin D1 was significantly increased in the animal experimental group 2 (P<0.01), and the increased expression of CDK4 and Cyclin D1 was significantly reduced in the animal experimental groups 3 and 4. In particular, the expression of CDK4 and Cyclin D1 was significantly lower in the animal experimental group 4 than the animal experimental group 3 (FIG. 9*c*, P<0.01~0.05).

In the stomach tissue of the animal experimental groups 1 to 4, the mucin content was confirmed by PAS staining, and the result was shown in FIG. 10. As shown in FIG. 10, the gastric mucin was observed at a significantly low level in the animal experimental group 2 (P<0.01), and the expression of gastric mucus was significantly preserved in the animal experimental groups 3 and 4, and the mucus expression was significantly higher in the animal experimental group 4 than 3 (P<0.01).

From the above result, it could be seen that WIRS threatened the mucosal integrity, but this threat was alleviated by pre-treatment of the composition (sample) according to one example.

The result of Examples 8 to 11 was represented by mean±SD. The data were analyzed by one-way analysis of variance (ANOVA), and the statistical significance between groups was determined by Duncan's multiple range test. The statistical significance converged to P<0.05.

From the above description, those skilled in the art to which the present application pertains will understand that the present application may be implemented in other specific forms without changing its technical spirit or essential characteristics. In this regard, it should be understood that the examples described above are illustrative in all aspects and not restrictive. The scope of the present application should be construed as the meaning and scope of the following claims rather than the above detailed description and all modifications or modified forms derived from the equivalent concept are included in the scope of the present application.

The invention claimed is:

1. A method of preventing, alleviating or treating a gastric disorder, comprising administering an effective amount of a composition comprising a fermented product obtained by culturing a *Corynebacterium* sp. strain in a medium, wherein the fermented product comprises the *Corynebacterium* sp. strain, and threonine produced by the *Corynebacterium* sp. strain, to a subject in need of preventing, alleviating or treating the gastric disorder, wherein the gastric disorder is gastrorrhagia caused by a stress-related mucosal disease;

wherein the composition comprises the threonine in an amount of 70 to 75% by weight; and wherein the *Corynebacterium* sp. strain is *Corynebacterium glutamicum.*

2. The method to claim 1, wherein the medium is a medium for producing threonine.

3. The method to claim 1, wherein the *Corynebacterium* sp. strain and its cultured product are comprised in a dried form.

* * * * *